(12) United States Patent
Carriazo

(10) Patent No.: US 6,551,306 B1
(45) Date of Patent: Apr. 22, 2003

(54) REFRACTIVE LASER ABLATION THROUGH TOPOGRAPHY

(76) Inventor: Cesar C. Carriazo, KRA 53 #82-202 Apto 5B, Barranquilla (CO)

( * ) Notice: Subject to any disclaimer, the term of this patent is extended or adjusted under 35 U.S.C. 154(b) by 0 days.

(21) Appl. No.: 09/290,756

(22) Filed: Apr. 13, 1999

(51) Int. Cl.⁷ ............................................... A61B 18/18
(52) U.S. Cl. ................................ 606/5; 606/4; 606/10; 606/12; 128/898; 351/212; 623/5.11
(58) Field of Search ........................ 606/4, 5, 6, 10–12, 606/13; 623/4–6; 351/211, 212

(56) References Cited

U.S. PATENT DOCUMENTS

| | | | | |
|---|---|---|---|---|
| 4,669,466 A | * | 6/1987 | L'Esperance ............ | 128/303.1 |
| 4,903,695 A | * | 2/1990 | Warner et al. .................. | 606/4 |
| 5,098,426 A | * | 3/1992 | Sklar et al. ..................... | 606/5 |
| 5,152,759 A | * | 10/1992 | Parel et al. ..................... | 606/5 |
| 5,163,934 A | * | 11/1992 | Munnerlyn .................... | 606/5 |
| 5,188,631 A | * | 2/1993 | L'Esperance et al. .......... | 606/5 |
| 5,196,006 A | * | 3/1993 | Klopotek et al. ............. | 606/12 |
| 5,196,027 A | * | 3/1993 | Thompson et al. ............ | 623/5 |
| 5,395,356 A | * | 3/1995 | King et al. ..................... | 606/4 |
| 5,505,723 A | * | 4/1996 | Muller ............................ | 606/5 |
| 5,514,124 A | * | 5/1996 | Alpins ............................ | 606/4 |
| 5,533,997 A | * | 7/1996 | Ruiz .............................. | 606/5 |
| 5,549,632 A | * | 8/1996 | Lai ................................ | 606/5 |
| 5,569,238 A | * | 10/1996 | Shei et al. ...................... | 606/4 |
| 5,571,107 A | | 11/1996 | Shaibani et al. | |
| 5,613,965 A | * | 3/1997 | Muller ............................ | 606/5 |
| 5,647,865 A | * | 7/1997 | Swinger ......................... | 606/5 |
| 5,741,245 A | * | 4/1998 | Cozean et al. .................. | 606/5 |
| 5,779,696 A | | 7/1998 | Berry et al. | |
| 5,782,822 A | * | 7/1998 | Telfair et al. ................... | 606/5 |
| 5,865,832 A | * | 2/1999 | Knopp et al. .................. | 606/10 |
| 5,984,916 A | * | 11/1999 | Lai ................................ | 606/11 |
| 6,099,522 A | * | 8/2000 | Knopp et al. .................. | 606/10 |
| 6,129,722 A | * | 10/2000 | Ruiz .............................. | 606/5 |

OTHER PUBLICATIONS

Richard K. Snook "Pachymetry and True Topography Using the ORBSCAN System" Date unknown but beleived to be prior art.*
David T.C. Lin, MD; Corneal Topographic Analysis After Excimer Photorefractive Keratectomy; Nov. 1993.
Schwind Opthalmic Technology; Keratom Excimer Laser; 1993.
Steven E. Wilson, MD Et Al.; Changes in Corneal Topography After Excimer Laser Photorefractive Keratectomy for Myopia; Oct. 1990.
Robert K. Maloney, MD; Corneal Topography and Optical Zone Location in Photorefractive Keratectomy; Jul. 13, 1990.
Sami G. El Hage, OD, PhD, Et Al.; Corneal Topography as Measured by the Eye Map EH–270; Date Unknown but Believed to be Prior Art.
Richard K. Snook; Pachymetry and True Topography Using the Orbscan System; Date Unknown but Believed to be Prior Art.
Werner Förster, MD Et Al.; Design and Development of a New 193–Nanometer Excimer Laser Surgical System; Jul. 1993.

* cited by examiner

*Primary Examiner*—Linda C. M. Dvorak
*Assistant Examiner*—Ahmed Farah
(74) *Attorney, Agent, or Firm*—Streets & Steets; Jeffrey L. Streets

(57) ABSTRACT

A method and system control the depth of corneal ablation during optical surgery by mapping the anterior and posterior surfaces of a patient's cornea to obtain full pachymetric topographical mapping of the patient's cornea. The patient's corneal pachymetric topographical mapping is used to identify a desirable corneal bed, and to guide a surgical laser in ablating a portion of the anterior surface of the patient's cornea to produce the desired corneal bed for appropriate vision correction.

27 Claims, 21 Drawing Sheets

REFRACTIVE LASER ABLATION THROUGH TOPOGRAPHY

BACKGROUND OF THE INVENTION

1. Field of the Invention

This invention relates generally to the field of ocular surgery, and more particularly to the use of excimer lasers for corneal refractive and therapeutic surgery.

2. Description of the Related Art

The use of excimer lasers in ocular surgery is today well known for performing corneal ablations with a high degree of accuracy. Applications of the excimer laser in refractive surgery include corrections of myopia, hyperopia, astigmatism, and presbyopia through the ablation of tissue on or within a patient's cornea. Thus, in photorefractive keratectomy (PRK), the aim is to flatten or steepen the central cornea to eliminate myopic, hyperopic, or presbyopic refractive errors and to correct corneal astigmatism. In phototherapeutic keratectomy, on the other hand, the intent is to smooth irregular corneal surfaces or remove opaque corneal tissue. A normal cornea is shown on the anterior portion of the eye, also known as the ocular globe, in FIG. 1.

The cornea includes five distinct layers, as seen in FIG. 2. Outermost layer 1 is the Epithelium, which is an anterior surface layer that promotes constant and active cellular reproduction. Second layer 2, known as the Bowman has a structural function of serving as an attachment means for the corneal epithelium. The Bowman layer adheres anteriorly to the epithelium and posteriorly binds to third layer 3, which is called the stroma. The stroma is the thickest layer, which gives body to the cornea. Fourth layer 4, called the Descemet, posteriorly bounds the stroma. The innermost and fifth layer 5 is known as the Endothelium, and includes a layer of immunological cells whose function is to pump-dehydrate the cornea and keep it transparent.

The excimer laser used for ocular surgery is typically a 193 nanometer Argon Fluoride surgical laser system, such as the Schwind Keratom System. FIG. 3 illustrates a schematic of laser beam delivery system 14 for the Schwind Keratom System. The Argon Fluoride excimer laser beam first passes through several optical components 18 where it is collimated and aligned to the eye to be treated. These optical components, which must be transparent for conducting the ultraviolet radiation of the beam, are made from a synthetic quartz such as Suprasil II.

Mechanical shutter system 16 controls the emission of the excimer laser beam. The shutter system consists of two independently actuated shutter blades that block the laser beam if the shutters are not energized. When the shutters are energized to permit passage of the laser beam, which is originally rectangular and exhibits a cross-section of approximately 8×24 mm, the beam is directed by 90-degree bending mirror 20 onto a specially designed optical component called an integrator, referenced as 22. The integrator homogenizes the laser beam energy over its cross-section.

The uniform and homogenous rectangular laser beam is then passed through a series of beam-stops 24 on moving steel band 26 to create the intended diameter of the laser beam. After passing the beam-stops, the laser beam is bent downwardly by dicroitic beam-splitter 28 for presenting the beam to the fixation target, the patient's cornea 10. The beam-splitter also permits the patient's eye to be observed via video camera 30, as indicated in FIG. 3.

After exiting beam splitter 28, the laser beam passes through another lens system 32 before hitting the patient's cornea. The lens system consists of two large-diameter lenses that produce an image of the beam-stop onto the patient's cornea. These lenses thus act like a zoom projection system.

The operation of integrator 22, steel band 26 with beam-stops 24, and zoom projection system 32 is computer controlled for precise variation of the corneal ablation diameter, typically over a range as wide as 0.6 to 8.0 mm. The corneal ablation results from the energy and wavelength of the laser beam, which disrupts the bond between molecules in the cornea and destroys corneal tissue in a controlled manner.

The system does not work in the same way for phototherapeutic keratectomy and photorefractive keratectomy. For phototherapeutic keratectomy, the surgeon selects a certain diameter of the ablation zone. This means that only one aperture of the steel band is used, and that the two large-diameter lenses do not move during the ablation process.

In the photorefractive keratectomy mode, however, the computer-controlled system changes the laser fluence during the treatment, depending on the selected steel band aperture and the position of the zoom optic. The zoom range and the available diameters of the beam-stops are designed so that a continuous variation of the ablation diameter of the cornea should be possible. For example, a simple myopic ablation of the patient's cornea may be achieved by a computer controlled combination of changes of different beam-stops and movements of the two large-diameter lenses.

Surgical lasers, such as the Schwind Keratom system, are controlled with the aid of nomograms that are based upon numerous studies and data bases. Such nomograms allow for appropriate correction of refractive defects in most patients, once the patient's particular gradation of myopia, hyperopia, astigmatism, or presbyopia has been identified through keratometric and subjective examination.

Refractive corneal surgery with an excimer laser is presently conducted in one of two ways: photorefractive keratectomy (PRK), shown in FIG. 4, and Laser In situ Keratomileusis (LASIK), shown in FIG. 5.

In the PRK technique, laser beam 40 is applied directly to the patient's corneal surface 10 according to the particular refractive defect. The laser system thus destroys an anterior portion of the cornea according to the machine's nomogram, leaving the stroma uncovered and resulting in the change shown at 42 in FIG. 4A. The stroma will later be covered with new Epithelial cells during the healing process, which takes a few days. One of the shortcomings of the PRK technique is that the Bowman layer or membrane is destroyed by the direct corneal application of the laser beam. The destruction of the Bowman layer is a major concern due to that layer's role in maintaining corneal transparency while serving as point of adhesion for the epithelium.

The LASIK technique involves the use of a microkeratome (not shown), which makes an access cut across the anterior portion of the cornea. More specifically, the microkeratome makes a lamellar resection of the cornea to create a corneal flap and hinge, as seen in FIG. 5. Flap 44, also known as a "pediculado," includes corneal tissue from the Epithelium, Bowman, and anterior stromal layers. The corneal flap is typically circular, having a diameter between 7 and 9 mm, and averages about 160 microns in thickness. A presently preferred microkeratome is described in pending U.S. application Ser. No. 09/002,515, the entire contents of which are incorporated herein by reference.

The corneal flap allows corneal stroma 3 to be exposed for ablation by laser beam 40 that is appropriate to correct the patient's refractive defect, as indicated in FIG. 5A. This results in altered stromal region 46 shown in FIG. 5B. Following the laser application, corneal flap 44 is returned to its initial position, as shown in FIG. 5C, and, since no ablation has been performed at the corneal surface, the patient suffers no destruction of the Bowman layer and recovers very rapidly.

A technique similar to the present-day LASIK procedure was described as early as Jun. 20, 1989 in U.S. Pat. No. 4,840,175 to Gholam A. Peyman. The '175 patent teaches the use of an excimer laser to modify the curvature of a patient's cornea. A thin layer of the cornea is removed "by cutting" (no details are provided), and a laser beam is then applied to either the thin layer or the exposed corneal surface. A variable diaphragm is used to form the laser beam into a desired predetermined pattern for ablation of desired portions of the thin layer or exposed cornea. The '475 patent further discloses the formation of disc-shaped and annular-shaped ablations for decreasing and increasing the curvature of the cornea as is desired.

The LASIK technique is particularly described for correction of presbyopia in U.S. Pat. No. 5,533,997. The '997 patent describes the use of a "corneal shaper," a particular microkeratome, in combination with an excimer laser to first resect at least a portion of the patient's cornea and then ablate an annular portion of the exposed stroma. The annular ablation is formed either by directing the laser beam in a circular path or by placing a mask over the central area of the stroma.

It is also generally known that in the art of refractive surgery various types of corneal topographers are used for mapping various portions of the cornea. Thus, the use of corneal topographers can provide information on the surface configuration of the corneal tissue by taking advantage of the cornea's transparency and analyzing light reflection and refraction on the cornea. The information is provided as a color scale representation of the corneal surface(s) with different values for interpretation. Once interpreted, the topographical information is useful for detecting which corneal pathologies can be corrected and which are not correctable by present refractive surgery techniques, and also for centering the laser beam ablation on the patient's visual axis.

Corneal topographers also permit the study of the cornea after refractive surgery has been performed. The normal cornea is somewhat aspherical with one meridian being flatter than the other. The resulting topographical map is shaped like hourglass 50, as shown in FIG. 6. This may be contrasted with central circular pattern 52 of FIG. 6A resulting after surgery to correct for myopia, resulting oval pattern 54 of FIG. 6B after surgery to correct for astigmatism, and resulting periferical pattern 56 of FIG. 6C after surgery to correct for hyperopia.

FIG. 7 illustrates an example of a particular corneal condition, called Corneal Ectasia and referenced at 58, in which the Stroma contains anomalous collagen which prevents the cornea from maintaining the normal aspherical shape and causes asymmetrical refractive defects that are very difficult to correct with glasses or contact lenses. Such Corneal Ectasia is virtually impossible to correct with either PRK or LASIK because these techniques further weaken the already distressed corneal structure.

Other corneal defects, including Leucoma scars (FIG. 8) and/or surface irregularities (FIG. 9) have not been successfully treated with conventional methods. Such defects have, for example, been treated by conventional manual resection, using a spatula or knife, of the anterior portions of the afflicted cornea and grafting tissue from a donor cornea onto the ablated area. These techniques, called Lamellar Keratoplasty or Homoplastic Lamellar Keratomileusis, spare the descemet or endothelium layers, since these layers are not affected by such pathologies. However, Lamellar Keratoplasty has lately been abandoned for use in these pathologies, because opacities and/or irregularities are typically left on the contact surfaces between the donor graft and the receiver stromal bed which prevent the patient from obtaining adequate vision recovery.

Patients suffering from corneal ectasia, leucoma scars, thin areas or corneal irregularities may otherwise find adequate vision correction through penetrating or deep keratoplasty, which is a total corneal depth transplant. Thus, the entire cornea is removed, including all five layers, and is replaced with an entire donor cornea as indicated in FIG. 10.

Several dangers and disadvantages are at risk when performing a deep keratoplasty, including the following:

1. the donor cornea must be fresh and contain a high number of active endothelial cells, since these cells are responsible for pump-dehydrating the cornea and also ensuring the final transparency of the graft tissue;
2. the complete healing of the donor graft requires approximately six months, during which time the sutures should not be removed;
3. the graduation of astigmatism is generally high, and can increase depending on the tension with which the sutures are left in place;
4. there is a relatively high likelihood of the donor graft failing and experiencing opacification due to endothelial rejection; and
5. it is an invasive technique involving perforation of the ocular globe, and thus presents danger of intraocular structural damage, loss of vitreo, intraocular infection, and in the worst case expulsion of the eye contents.

To address these disadvantages and shortcomings in the art, it is a principal object of the present invention to provide a surgical method that is based upon information about the shape of the corneal structure rather than merely the refractive defect identified by keratometric and subjective examination.

It is a further object of the present invention to combine corneal topography systems, particularly elevation or altitude topographers, with excimer laser systems to perform corneal ablation based on information regarding the corneal anterior and posterior surfaces.

It is a further object of the present invention to achieve the ablation of greater amounts of tissue in some corneal areas and smaller amounts of tissue in other corneal areas, as indicated by elevation topography.

It is a further object of the present invention to ablate a portion of the cornea so as to leave the posterior layers of the cornea with an even thickness.

It is a further object of the present invention to achieve corneal ablation while protecting the descemet and endothelium layers.

It is a further object of the present invention to allow the performance of a Lamellar Keratoplasty that achieves a known, smooth, accurately estimated stromal bed that prevents irregularities in the final outcome such as opacities of the contact surfaces between the donor and receptor surfaces.

SUMMARY OF THE INVENTION

The objects described above, as well as various other objects and advantages, are achieved by a method and system for controlling the depth of corneal ablation during optical surgery. The method and system contemplate the steps of mapping the anterior and posterior surfaces of a patient's cornea to obtain full pachymetry of the patient's cornea. The patient's corneal pachymetry is used to identify a desirable corneal bed, and to guide a surgical laser in ablating a portion of the anterior surface of the patient's cornea to produce the desired corneal bed.

The corneal pachymetry may be used to identify whether the cornea exhibits refractive defects, therapeutic defects, or both.

The depth control method and system of the present invention contemplates the desirable corneal bed being substantially beneath a defective portion of the cornea, whereby ablation of the defective portion of the cornea would expose the desirable corneal bed.

The surgical laser is guided so that the resulting ablated portion of the patient's cornea may exhibit either a constant thickness or a variable thickness as determined by the patient's corneal pachymetry. In this fashion, the thickness may be varied for correction of myopia, hyperopia, astigmatism, ectasia, leucoma, or corneal surface irregularities.

The above-described method and system may be useful in various applications, such as lamellar keratoplasty or deep keratoplasty. In such applications, a corneal disc is ablated from the anterior surface of a recipient cornea in such a manner that the donor corneal disc has a similar diameter and thickness to the ablated portion of the patient's cornea, or a known, greater, or lesser diameter, as the surgeon may determine for that specific patient. The donor corneal disc is then placed onto the produced desired corneal bed of the patient's cornea.

It is preferred, in applications such as lamellar keratoplasty or deep keratoplasty, that the thickness of the ablated portion of the patient's cornea is designed such that the descemet and endothelium layers of the cornea are left intact.

It is also preferred in the above-described method and system that the mapping step be accomplished with an elevation-type corneal topography system, such as the ORB-SCAN topography system.

The present invention further contemplates a method and system of ocular surgery that improves on the LASIK procedure given that it can be performed on patients that would not otherwise be candidates for LASIK. First, the anterior and posterior surfaces of a patient's cornea are mapped to obtain full pachymetry of the patient's cornea. A desirable corneal bed is identified using the patient's corneal pachymetry. The patient's ocular globe is secured, and on the basis of the topographical information, an ablation is made with the laser of the amount of tissue to be removed in order to obtain a known adequate corneal bed. The procedure is completed by replacing a lamellar or total known thickness and known diameter donor cornea on the bed so prepared.

BRIEF DESCRIPTION OF THE DRAWING(S)

So that the manner in which the above recited features, advantages and objects of the present invention are attained can be understood in detail, a more particular description of the invention, briefly summarized above, may be had by reference to the preferred embodiment thereof which is illustrated in the appended drawings.

It is to be noted however, that the appended drawings illustrate only a typical embodiment of this invention and are therefore not to be considered limiting of its scope, for the invention may admit to other equally effective embodiments.

DESCRIPTION OF THE PREFERRED EMBODIMENT(S)

Figure 11:
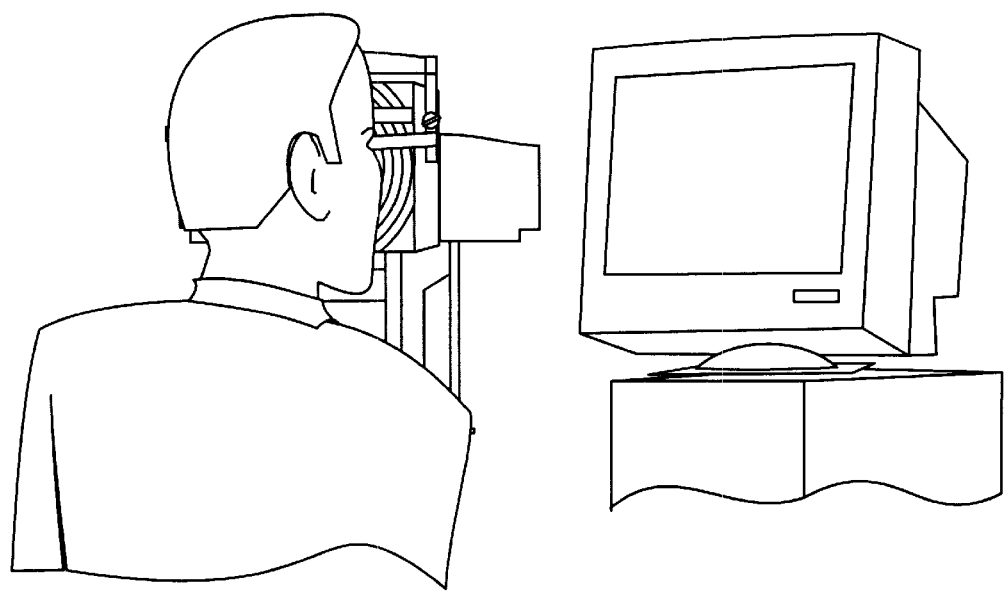
FIG. 11 illustrates the ORBSCAN topography system.

The surgical ablation depth control method and system of the present invention contemplate the step of mapping the anterior and posterior surfaces of a patient's cornea to obtain full pachymetry of the cornea. It is preferred that the mapping step be accomplished with an elevation-type corneal topography system, such as the ORBSCAN topography system depicted generally in FIG. 11.

The ORBSCAN system employs a calibrated video and scanning slit beam to non-invasively and independently measure 3-dimensional space (x, y, and z) locations of several thousand points on the anterior and posterior surfaces of the cornea. These locations are used to construct mathematical topographical maps of the elevation (z) versus the horizontal (x) and vertical (y) components for the two corneal surfaces. These mathematical representations have second-order derivatives, and are differentiated to calculate the slope and curvature at any point and in every direction along the corneal surface. Differences between the surface locations yield various corneal thickness and depths, along with the surface normal thickness known as the corneal pachymetry.

Figure 12:
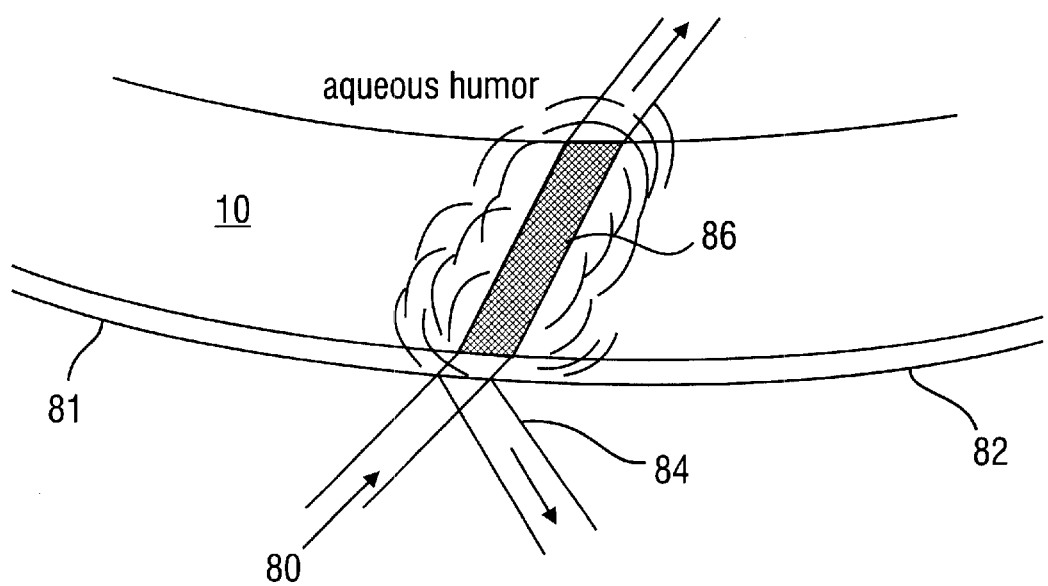
FIG. 12 is a schematic representation of specular and diffuse reflection resulting from the application of a slit beam to the cornea using the ORBSCAN system.
Figure 13:
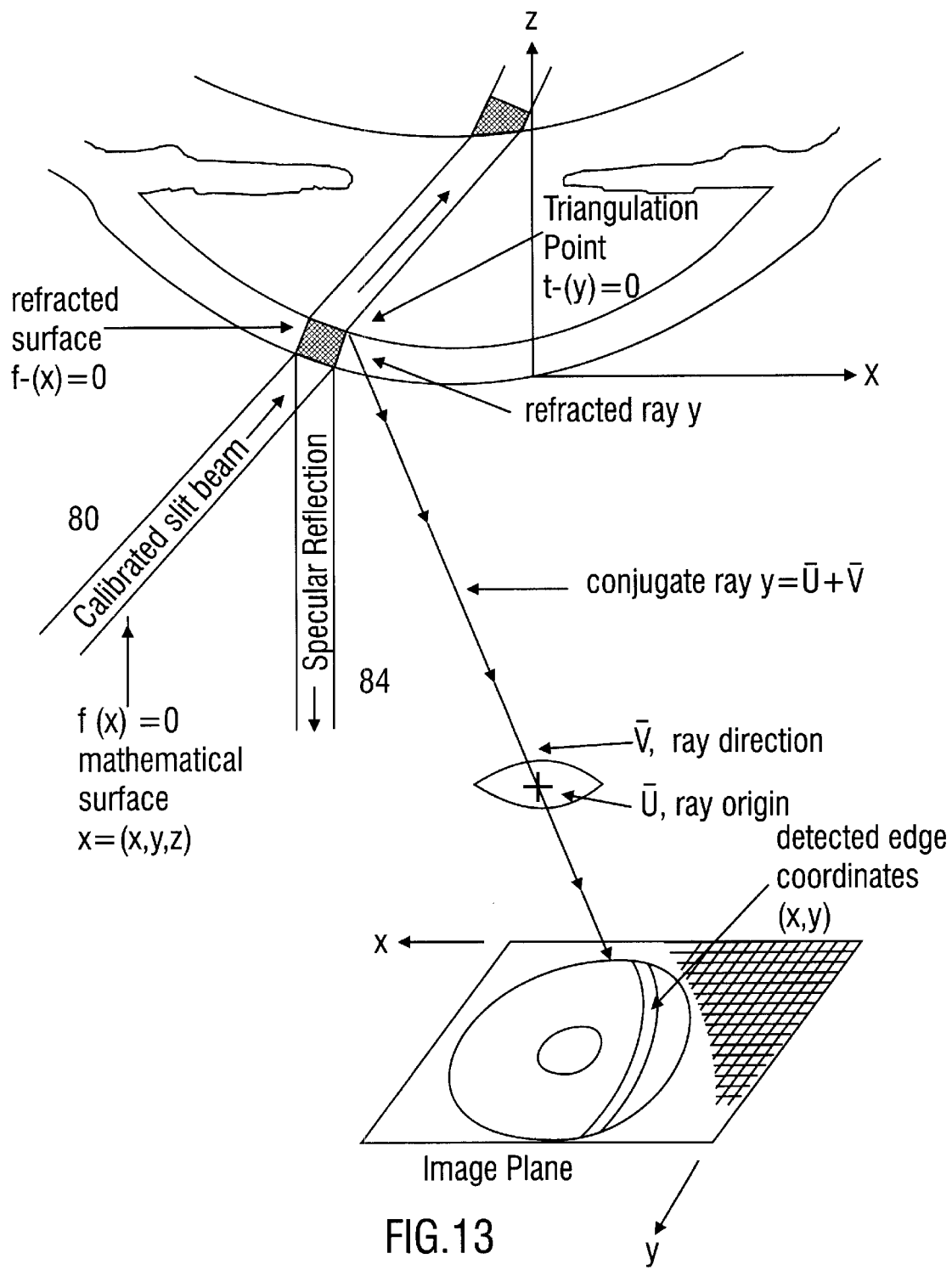
FIG. 13 is a schematic representation of ray-trace triangulation as used by the ORBSCAN system for mapping the corneal surfaces.

The principal of the scanning slit beam is illustrated in FIGS. 12 and 13. When slit beam 80 intercepts smooth anterior surface 81 of cornea 10, it splits into specular reflection 84 and refracted beam 86 that penetrates the anterior surface and is volume scattered in all directions by internal "scattering centers" in the corneal, as indicated in FIG. 12. This volume scattering allows points on the anterior surface to be independently observed and triangulated, and gives the ORBSCAN device the ability to measure arbitrary surface shapes (convex, concave, aspherical, or irregular). The magnitude of volume scattering is typically negligible from liquids like tear film 82 and the aqueous humor, but is significant from the relative large collagen fibers in the corneal stroma. As a result, diffusely reflected images, which are projections of the scattering volume illuminated by the slit beam, are visible through the tear film and aqueous humor.

Since typical internal scatters are generally smaller than the wavelength of visible light, the magnitude of scattering is inversely proportional to the third or fourth power of the optical wavelength (Raleigh scattering). Thus, the diffusely scattered return consists of the shortest wavelengths found in the original beam, and corneal backscatter generally appears blue.

The planar slit beam, diffusely reflected from the convex shell of the cornea, appears as an annular arc in a video image of the cornea. The outer and inner edges of this arc respectively correspond to the anterior and posterior surfaces of the illuminated corneal volume.

To locate a point on the anterior surface, an outer edge point is first detected to sub-pixel accuracy. From the video calibration, the detected edge point is then translated into the chief ray that entered the camera and formed the image. The camera ray is mathematically intersected with the slit beam surfaces, which are precisely located during the calibration process. The result of this process, known as direct triangulation, is an anterior corneal surface point located in 3-dimensional space (x,y,z).

Ray-trace triangulation, shown in FIG. 13, is required when a surface point lies behind an optical interface that reflects the slit beams and the camera rays of the edge points. As ocular surfaces are triangulated one at a time from front to back, all the refracting surfaces in front of a desired surface point are known a priori and can be used to calculate all the necessary optical refractions. The result is an undistorted measurement of an internal ocular surface.

Figure 1:
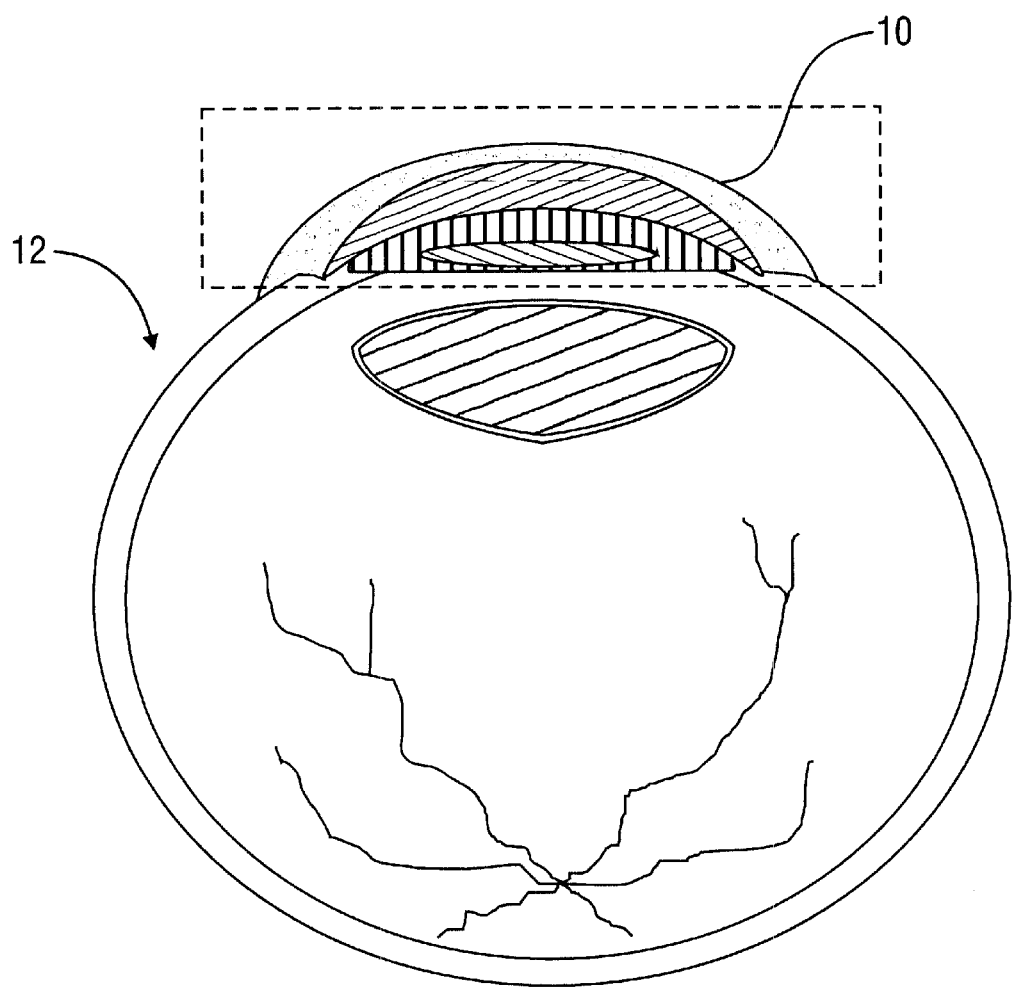
FIG. 1 is a plan view of a normal eye, taken in cross-section, with emphasis on the cornea.
Figure 2:
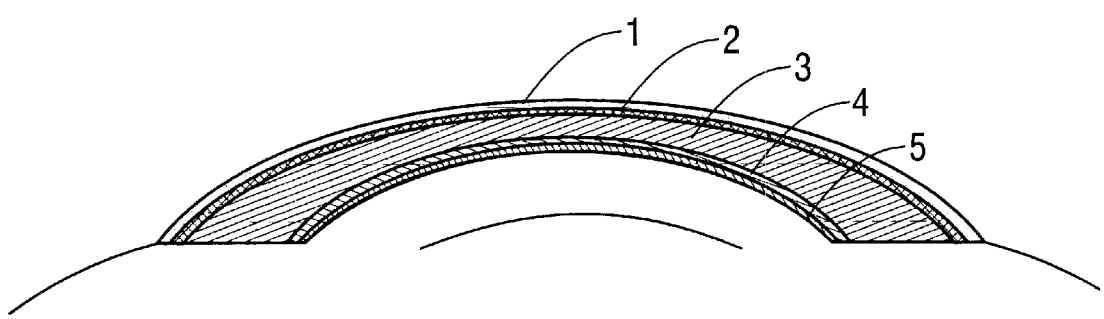
FIG. 2 is a detailed view of the corneal region and its five layers.
Figure 3:
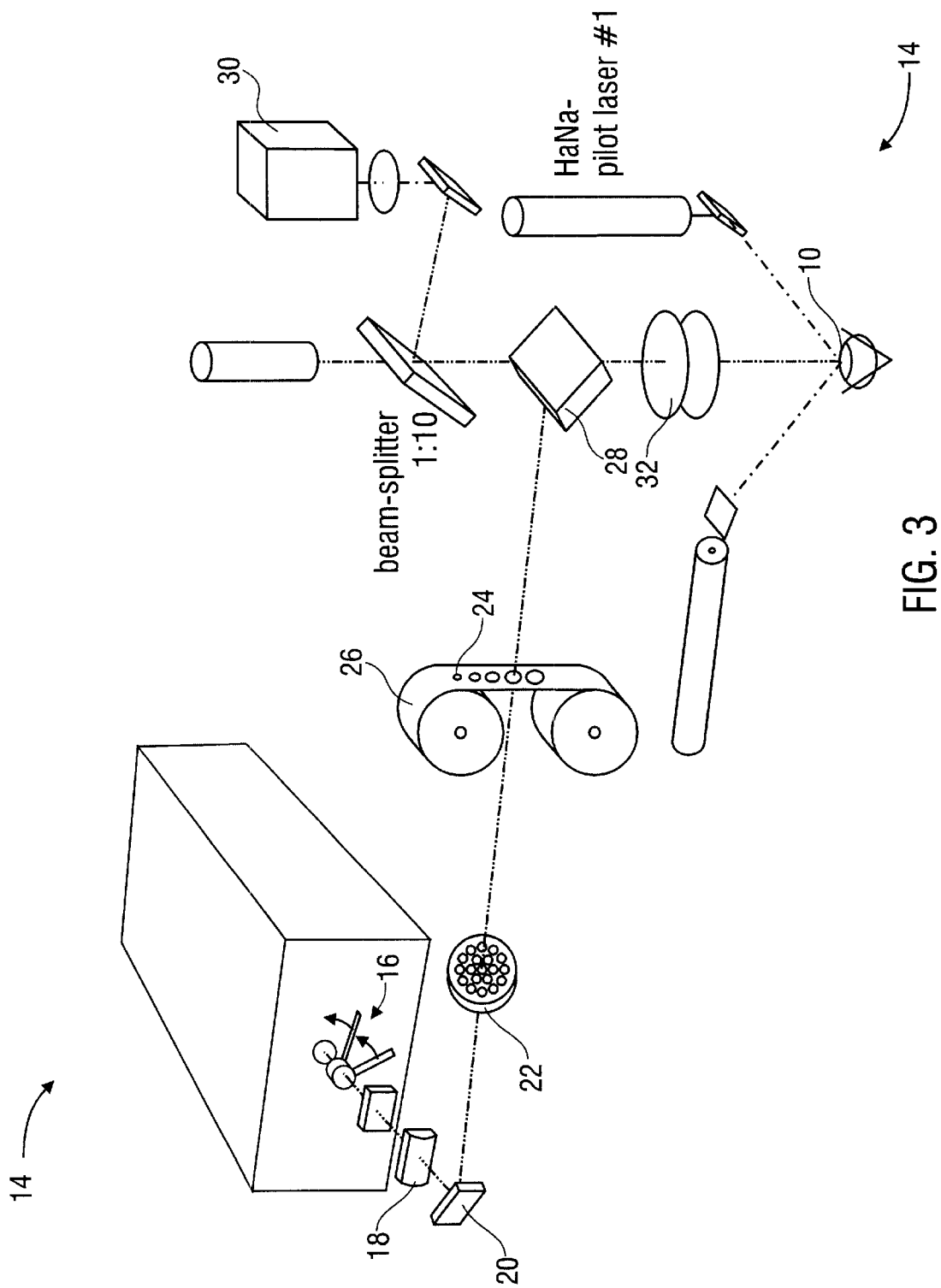
FIG. 3 is a schematic illustration of a laser beam delivery system for a particular excimer laser, the Schwind Keratom laser system.
Figure 4:
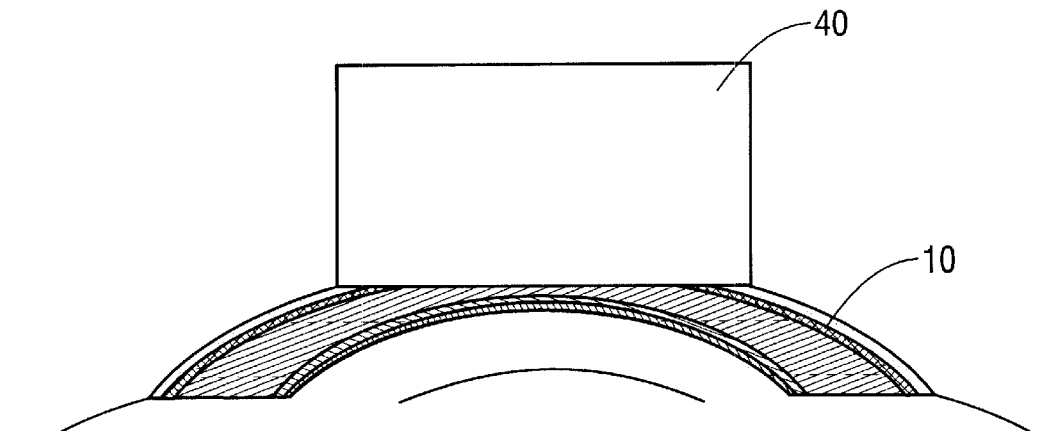
FIG. 4 shows a laser beam being applied to the corneal region during a photorefractive keratectomy (PRK) procedure.
Figure 4A:
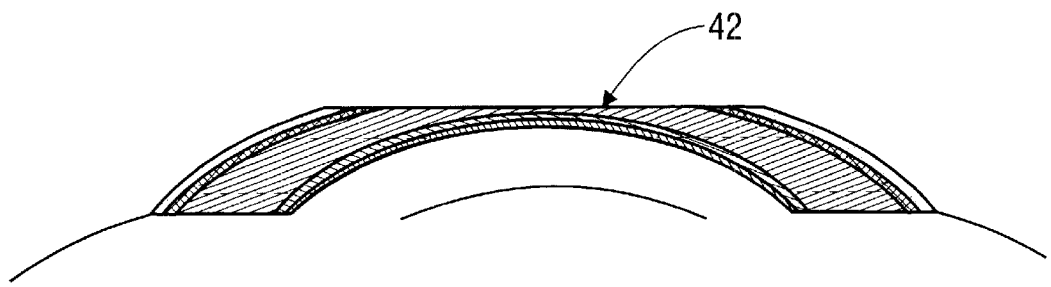
FIG. 4A shows the altered shape of the corneal region after a PRK procedure to correct myopia.
Figure 5:
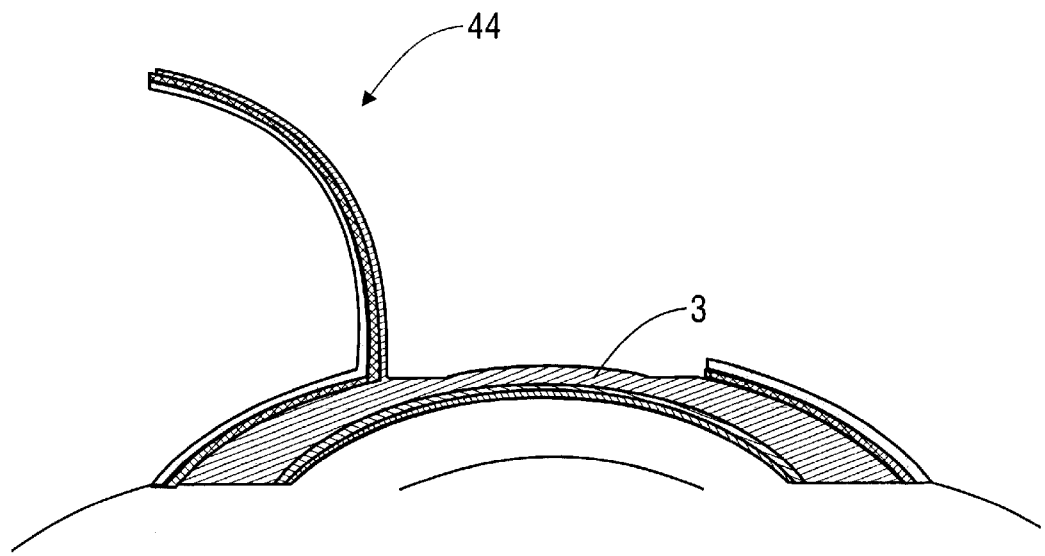
FIG. 5 illustrates a folded corneal flap and exposed stroma during a laser in situ keratomileusis (LASIK) procedure.
Figure 5A:
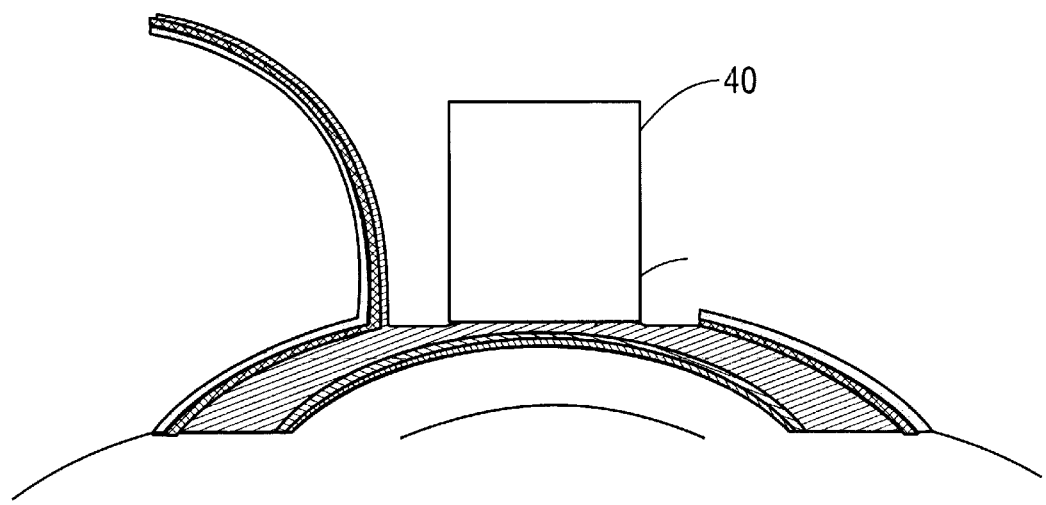
FIG. 5A illustrates the application of a laser beam to the exposed stroma during the LASIK procedure.
Figure 5B:
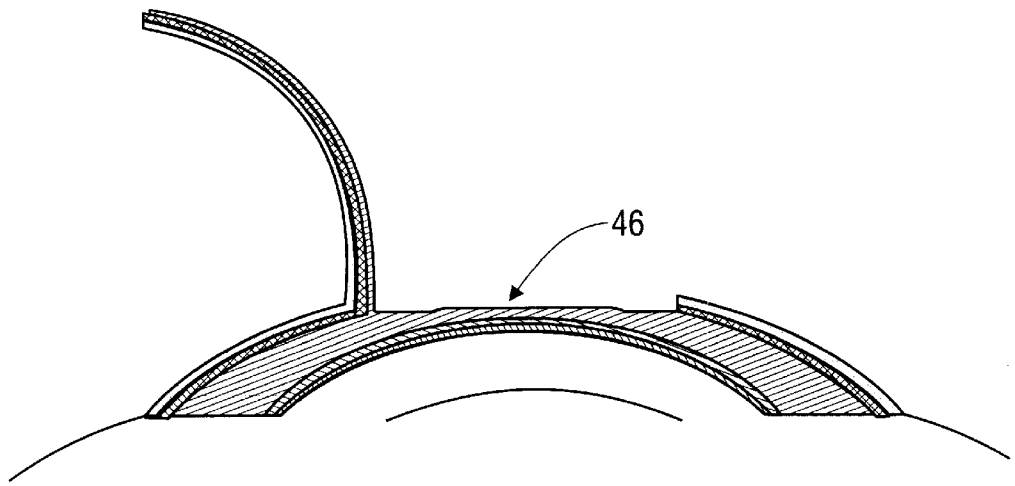
FIG. 5B shows the altered shape of the corneal region after laser ablation to correct myopia during the LASIK procedure.
Figure 5C:
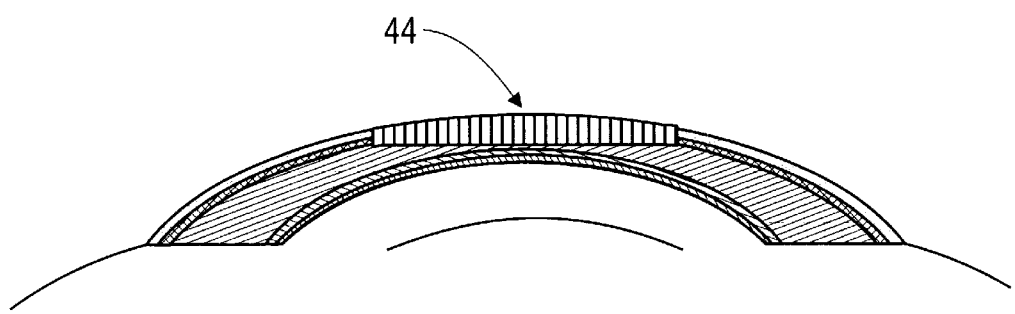
FIG. 5C shows the corneal flap returned to its initial position after completion of the LASIK procedure.
Figure 6:
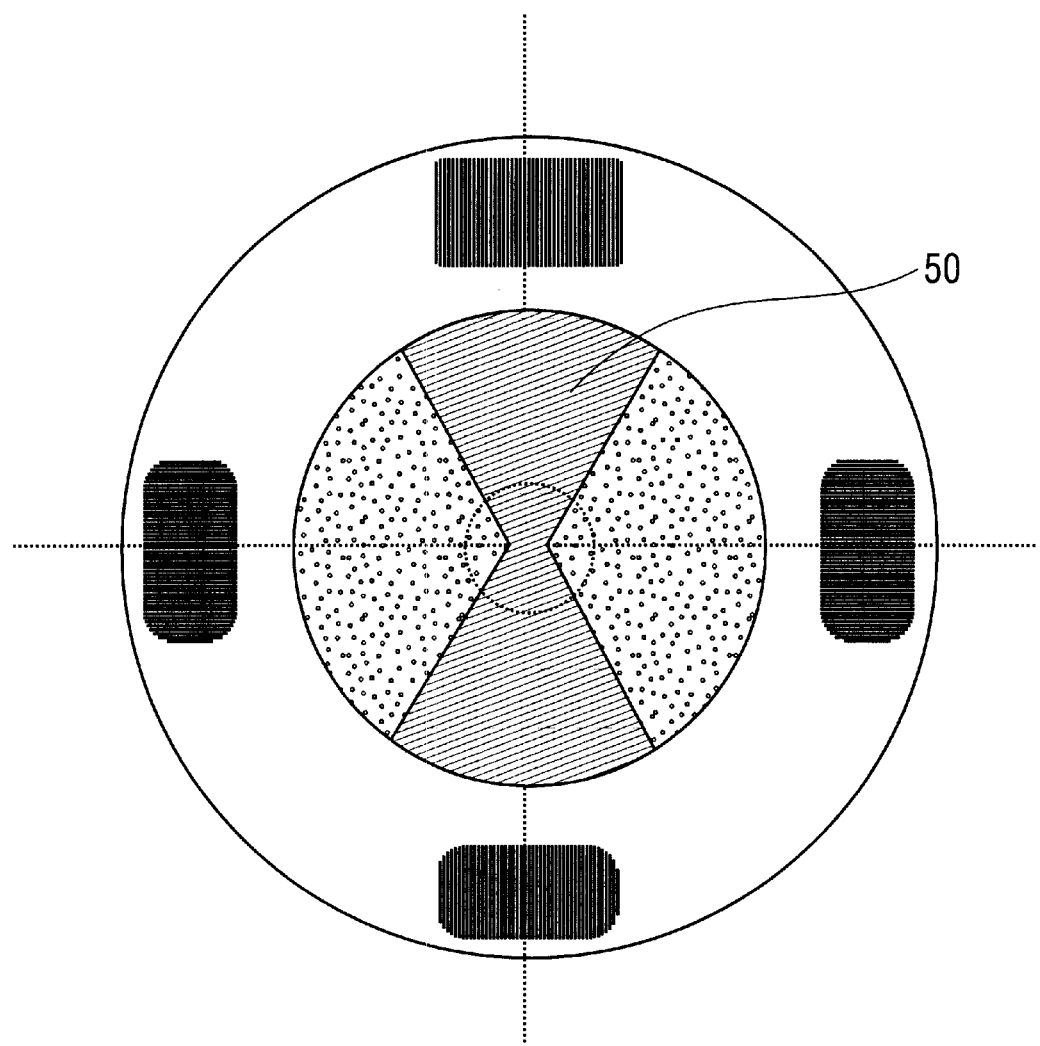
FIG. 6 is a topographical map of a normal cornea exhibiting an hourglass shape.
Figure 6A:
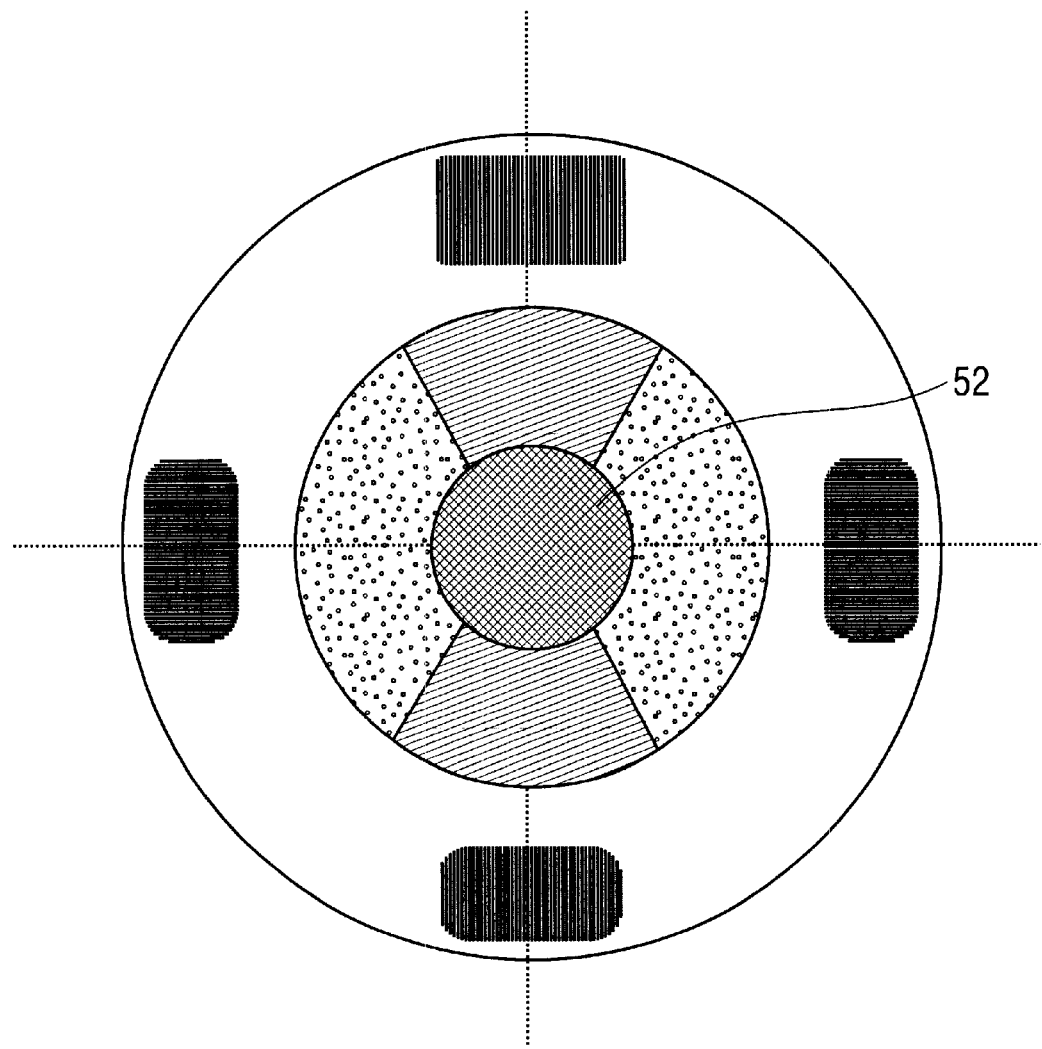
FIG. 6A is a topographical map of a cornea after surgical correction for myopia.
Figure 6B:
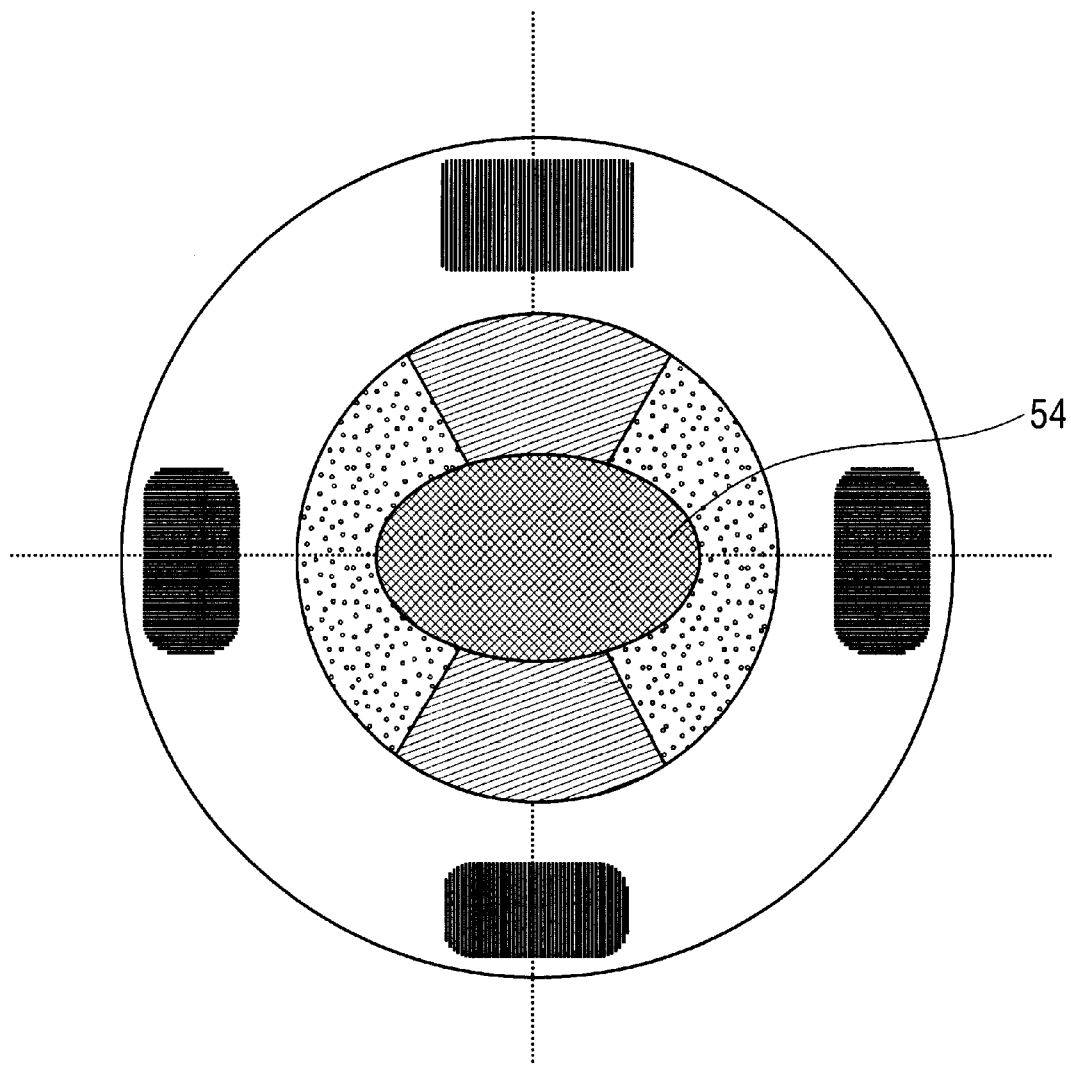
FIG. 6B is a topographical map of a cornea after surgical correction for astigmatism.
Figure 6C:
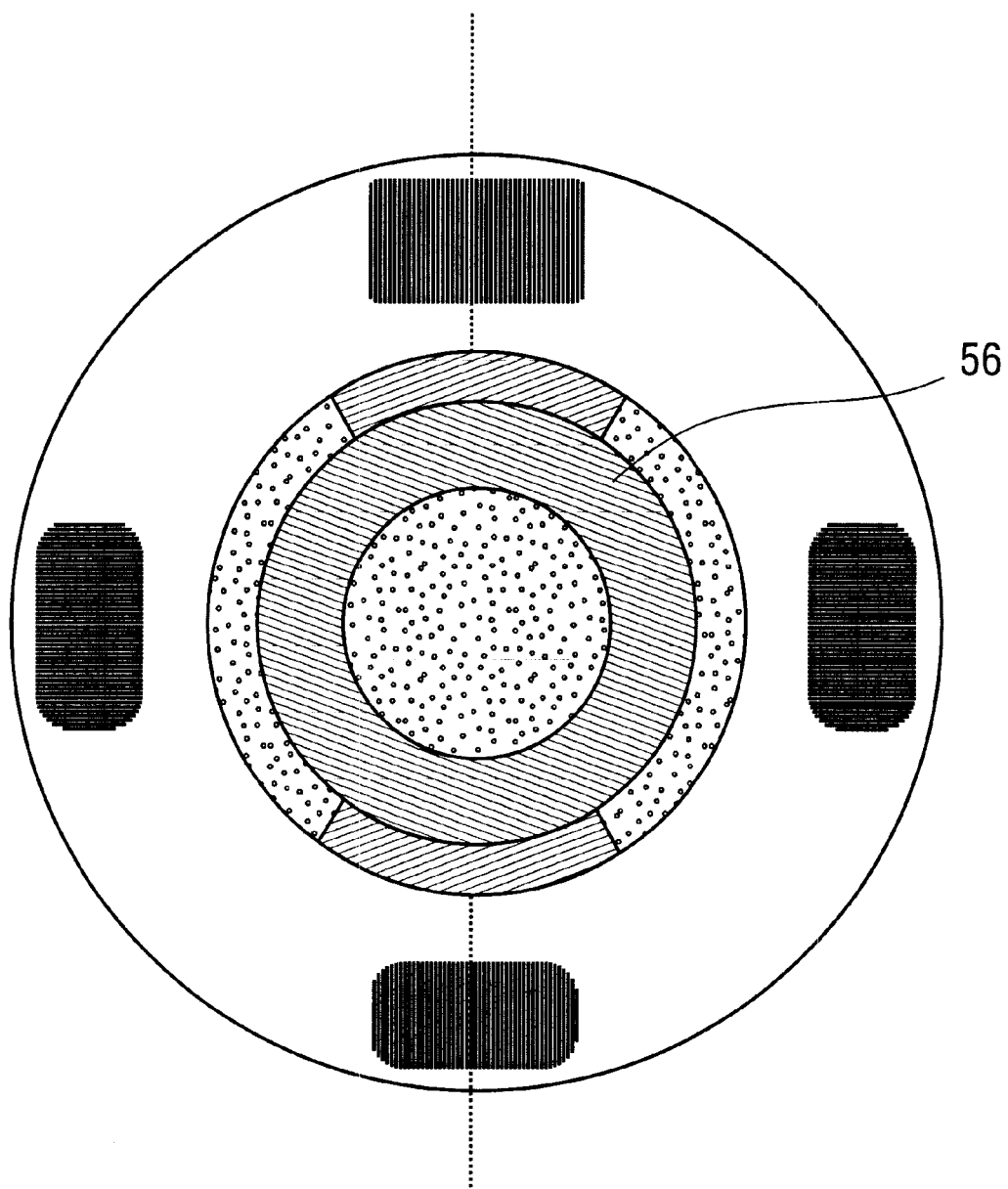
FIG. 6C is a topographical map of a cornea after surgical correction for hyperopia.
Figure 7:
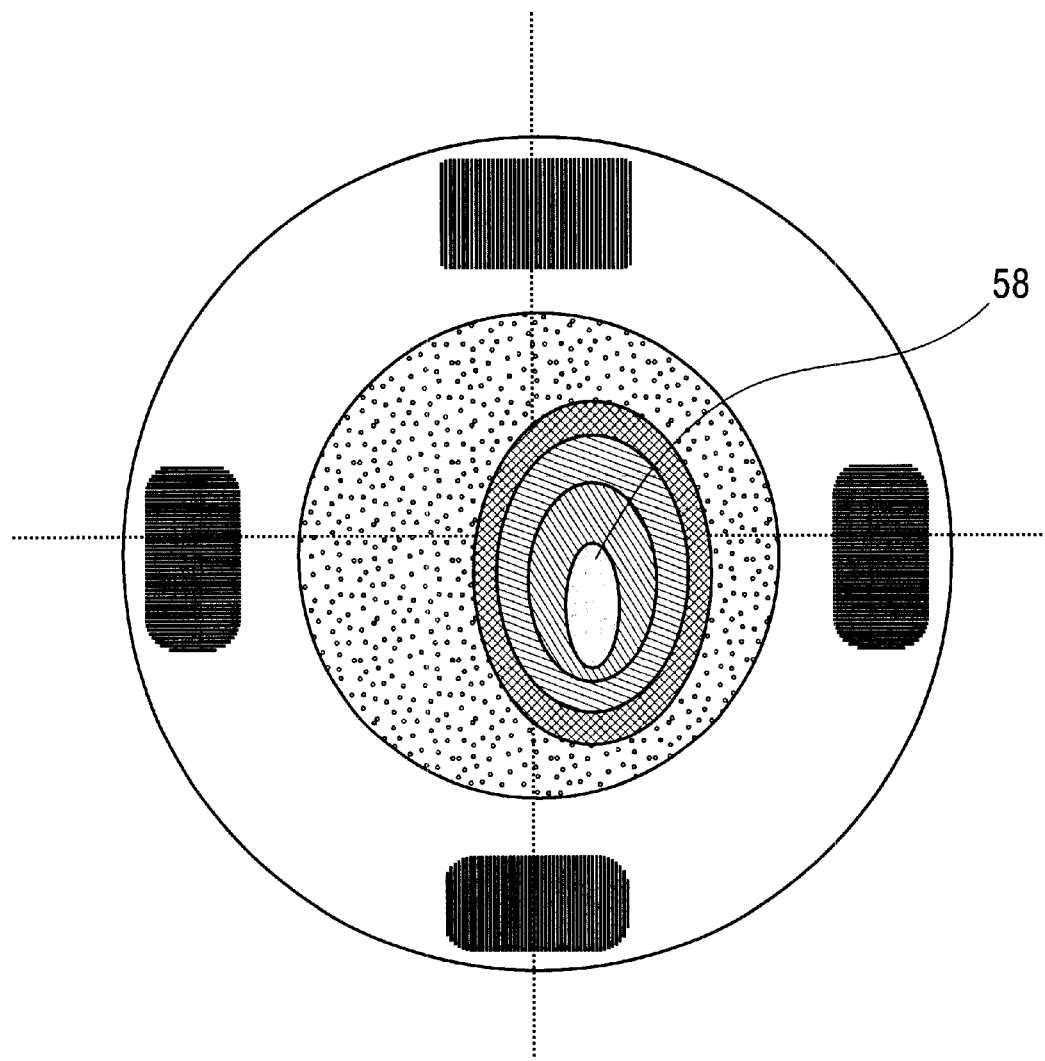
FIG. 7 is a topographical map of a cornea exhibiting a corneal ectasia.
Figure 7A:
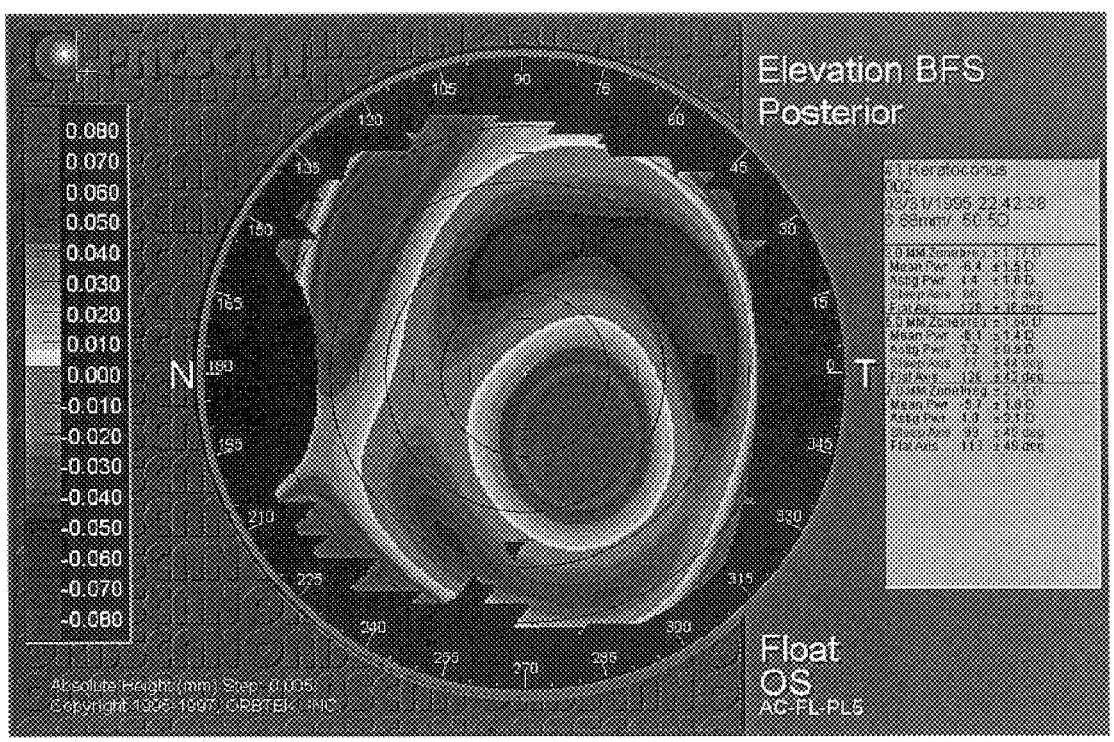
FIG. 7A is an elevation or altitude topographical map of a cornea exhibiting a corneal ectasia.
Figure 7B:
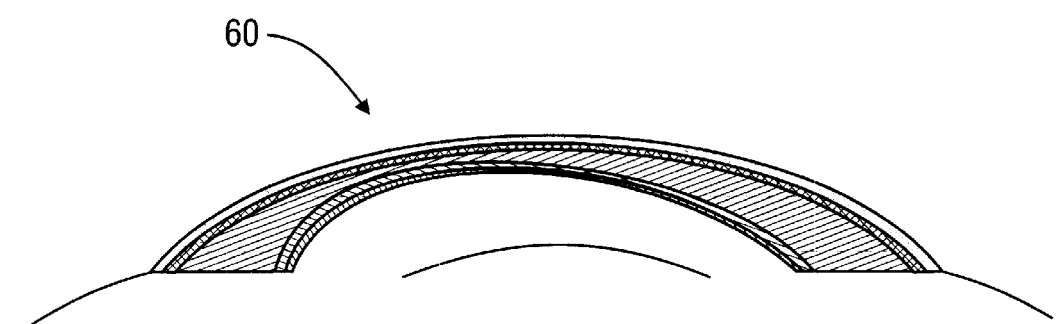
FIG. 7B is a plan view, taken in section, of a cornea exhibiting a corneal ectasia.

The ORBSCAN system thus provides elevation topographical maps of the anterior and posterior corneal surfaces. Elevation topography of the anterior cornea enables abnormal corneas to be more accurately visualized. This leads to better diagnosis and more consistent surgical results. Furthermore, full corneal pachymetry allows surgeons to measure laser ablation depth from a fixed surface, the posterior corneal surface The corneal pachymetry may be used to identify whether the cornea exhibits refractive defects, therapeutic defects, or both. By providing a map of the corneal thickness across the ocular globe, corneal pachymetry effectively provides a cross-sectional view of the cornea, such as that shown in FIG. 7B for a cornea exhibiting corneal ectasia 60.

The above-described method and system may be useful in numerous applications, such as lamellar keratoplasty or deep keratoplasty. In such applications, a corneal disc is ablated from the anterior surface of a donor cornea in such a manner that the donor corneal disc has a similar diameter and thickness to the ablated portion of the patient's cornea. The donor corneal disc is then placed onto the produced desired corneal bed of the patient's cornea. Those skilled in the art will appreciate that the donor cornea disk may also be sized to have a different diameter and/or thickness than the ablated portion of the patient's cornea, as determined by the surgeon.

Figure 7C:
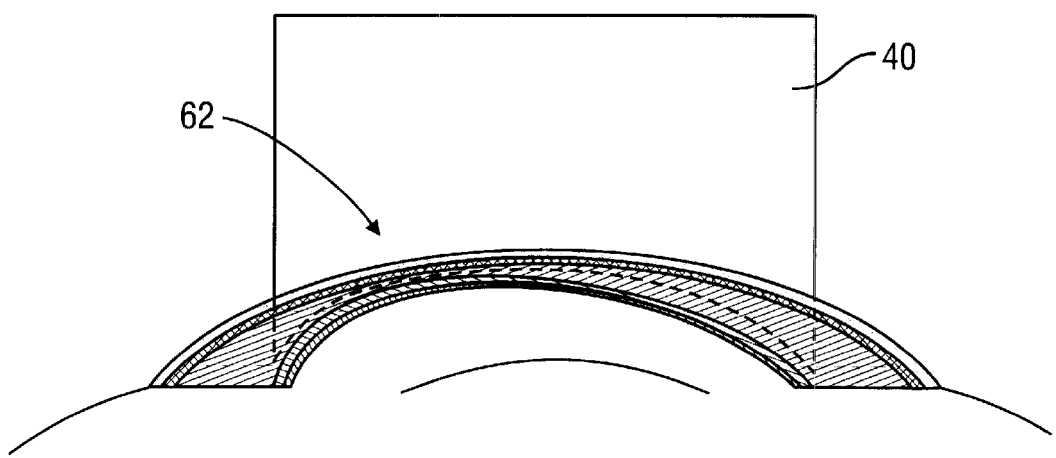
FIG. 7C illustrates the asymmetric application of a laser beam to the cornea of FIG. 7B.
Figure 7D:
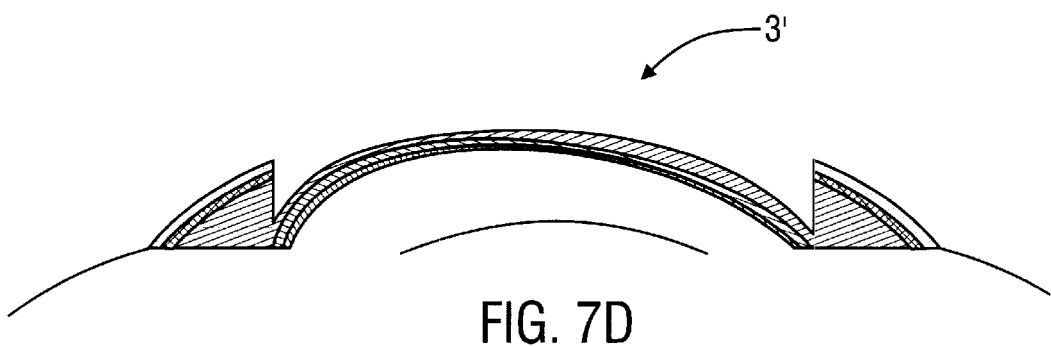
FIG. 7D shows the ablation resulting from the laser application of FIG. 7C, with the exposed stromal bed having a uniform thickness.

For a lamellar keratoplasty, the patient's corneal pachymetry is used to identify a desirable corneal bed, and to guide a surgical laser in ablating a portion of the anterior surface of the patient's cornea to produce the desired corneal bed. The depth control method of the present invention contemplates the desirable corneal bed being substantially beneath a defective portion of the cornea, whereby ablation of the defective portion of the cornea would expose the desirable corneal bed. FIG. 7C illustrates the asymmetric application of laser beam 40 to the cornea of FIG. 7B, wherein the laser is selectively controlled to ablate corneal tissue 62 to a greater or lesser extent across the eye as determined by the thickness of the cornea. This results in the ablation shown in FIG. 7D, wherein the exposed stromal bed 3' has a uniform thickness across the eye.

It is preferred, in applications such as lamellar keratoplasty or deep keratoplasty, that the thickness of the ablated portion of the patient's cornea is designed such that the descemet and endothelium layers 4, 5 of the cornea are left intact because these layers are responsible for the pumping action of the cornea and the immunological function of the cornea that prevents rejection of a donor graft. By utilizing the corneal pachymetry obtained from an elevation topographer, the depth of ablation is controlled to avoid laser penetration into these layers of the cornea. Through computer software, the data collected from the patient's topographical mapping is fed to the laser and through that same software a known ablation is performed to obtain a desirable, known corneal bed.

Thus, the surgical laser is guided in this instance so that the ablated portion of the patient's cornea exhibits a variable thickness. The laser may also be guided, however, so that the resulting ablated portion of the patient's cornea exhibits a constant thickness if the patient's corneal indicates that such ablation is desirable. In this fashion, the thickness or extent of the ablated tissue may be varied for correction of myopia, hyperopia, astigmatism, ectasia, leucoma, or corneal surface irregularities.

Figure 7E:
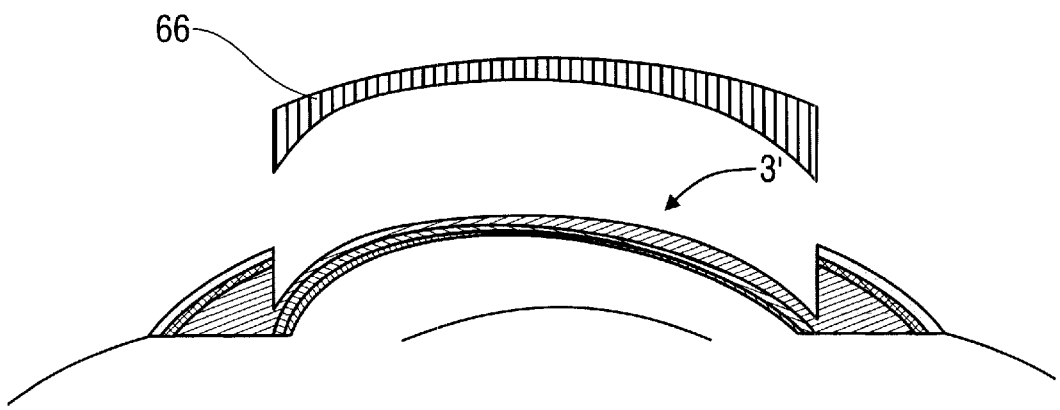
FIG. 7E shows a disc from a donor corneal being positioned for grafting onto the exposed stromal bed of the receiver cornea.
Figure 7F:
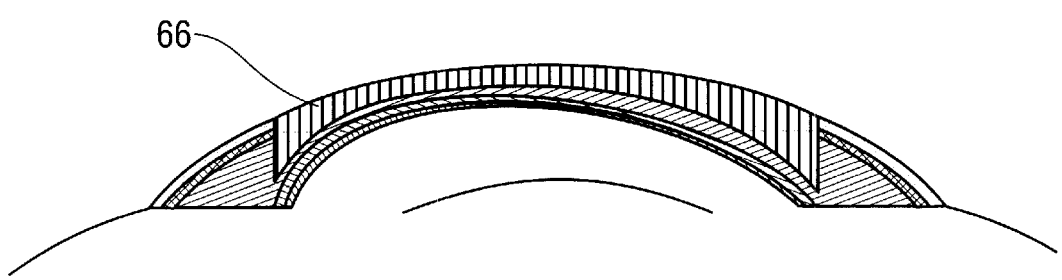
FIG. 7F shows the donor corneal disc positioned in place on the stromal bed of the receiver cornea.
Figure 7G:
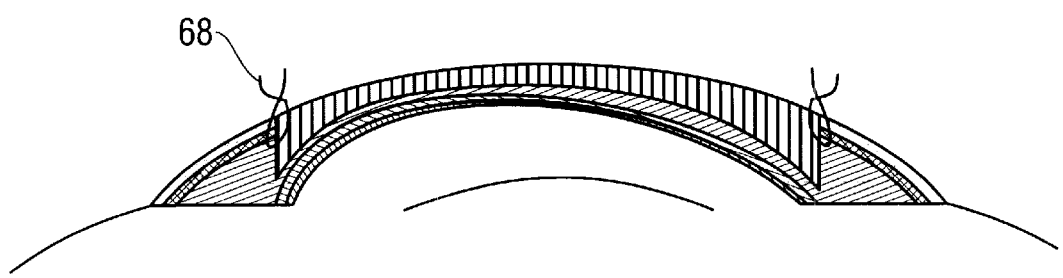
FIG. 7G shows the donor corneal disc sutured in place for healing.

FIG. 7E shows disc 66 ablated from a donor corneal being positioned for grafting onto the exposed stromal bed 3' of the receiver cornea. FIG. 7F shows the donor corneal disc positioned in place on the stromal bed of the receiver cornea, wherein the eye is restored to the desired shape for normal vision. FIG. 7G shows the donor corneal disc sutured in place with sutures 68 for healing.

Figure 8:
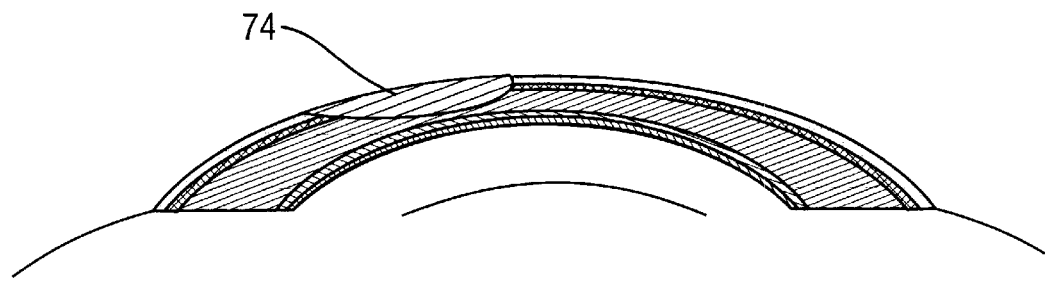
FIG. 8 is a plan view, taken in cross-section, of a cornea exhibiting a leucoma.
Figure 8A:
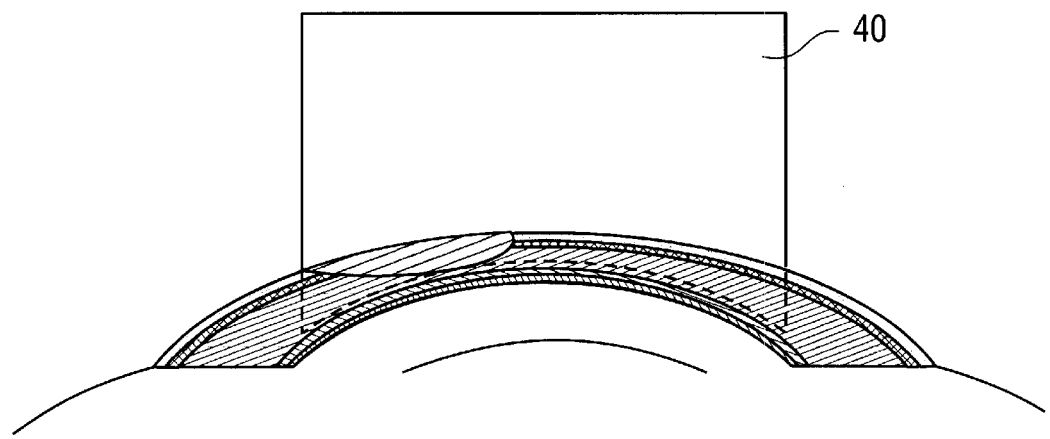
FIG. 8A shows the asymmetric application of a laser beam to the cornea of FIG. 8.
Figure 8B:
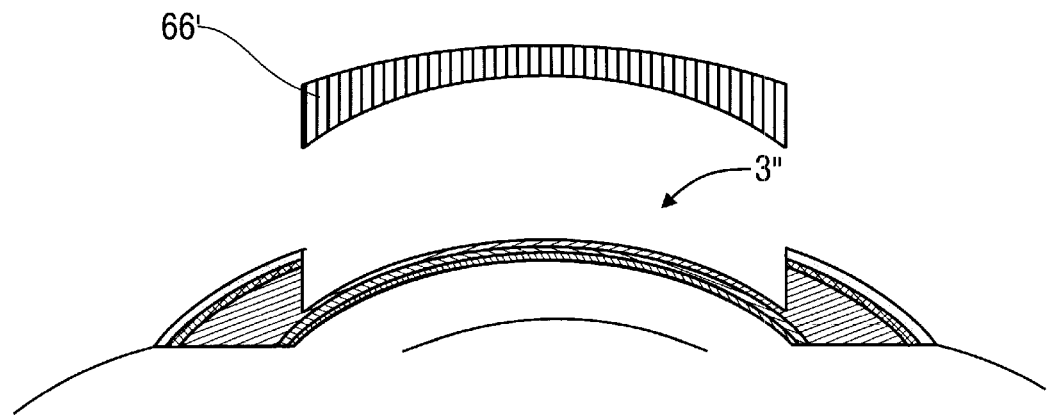
FIG. 8B shows the ablation resulting from the laser application of FIG. 8A, with the exposed stromal bed having a uniform thickness, and a disc from a donor cornea being positioned for grafting onto the exposed stromal bed.
Figure 8C:
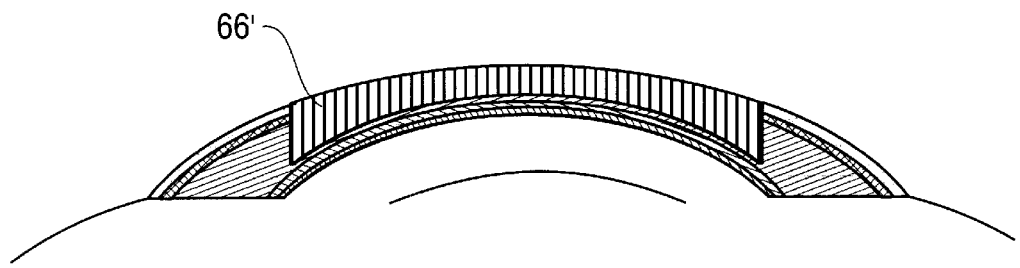
FIG. 8C shows the donor corneal disc positioned in place on the stromal bed of the receiver cornea.
Figure 8D:
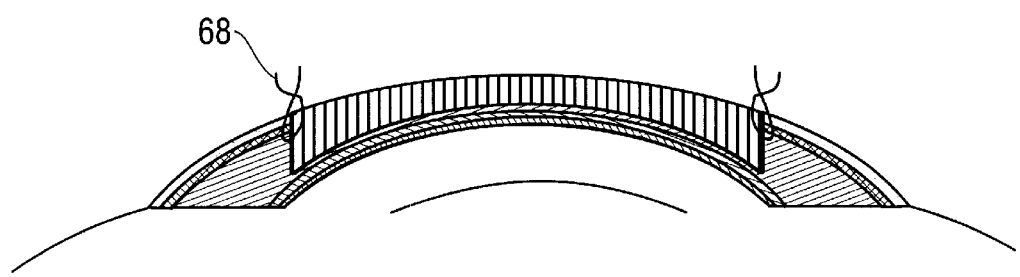
FIG. 8D shows the donor disc sutured in place for healing.

A lamellar keratoplasty procedure will now be described for correcting a leucoma or wound 74 on the patient's cornea, as shown in FIG. 8. FIG. 8A shows the asymmetric application of laser beam 40 to the cornea of FIG. 8. Again, the laser is guided by the patient's corneal pachymetry obtained from the elevation topographer so that the extent of ablation is safely varied across the eye. In this manner, the damaged tissue is entirely ablated but the descemet and endothelium layers of the cornea are left intact. The resulting ablation exposes corneal stromal bed 3" having a uniform thickness, as shown in FIG. 8B. This figure also shows disc 66' ablated from a donor cornea being positioned for grafting onto the exposed stromal bed. In FIG. 8C, the donor corneal disc has been positioned in place on the stromal bed of the receiver cornea. The procedure is completed in FIG. 8D, which shows the donor disc sutured in place with sutures 68 for healing.

Figure 9:
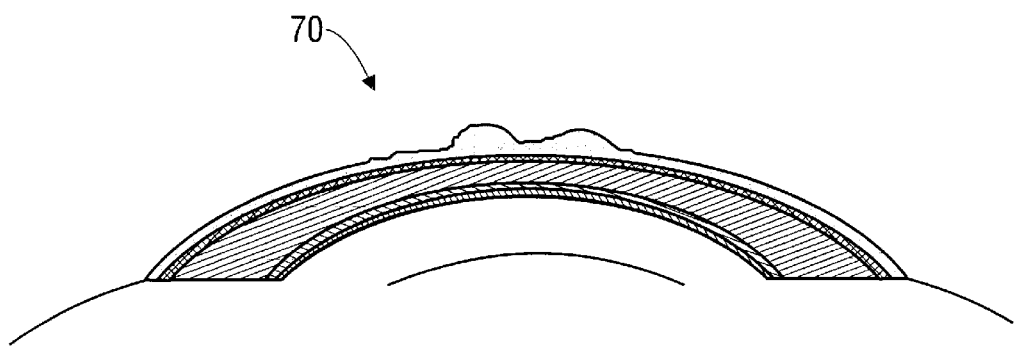
FIG. 9 is a plan view, taken in section, of the cornea exhibiting surface irregularities.
Figure 9A:
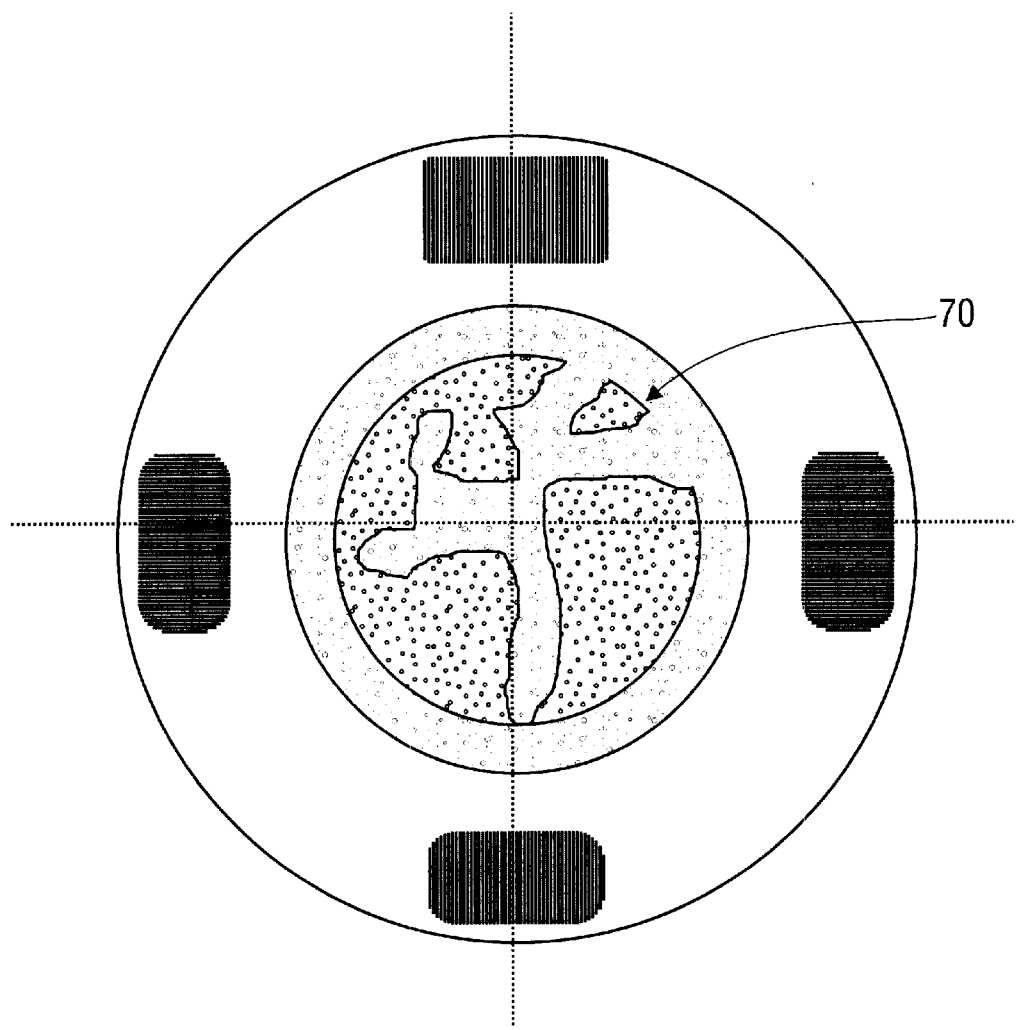
FIG. 9A is topographical map of the cornea of FIG. 9.
Figure 9B:
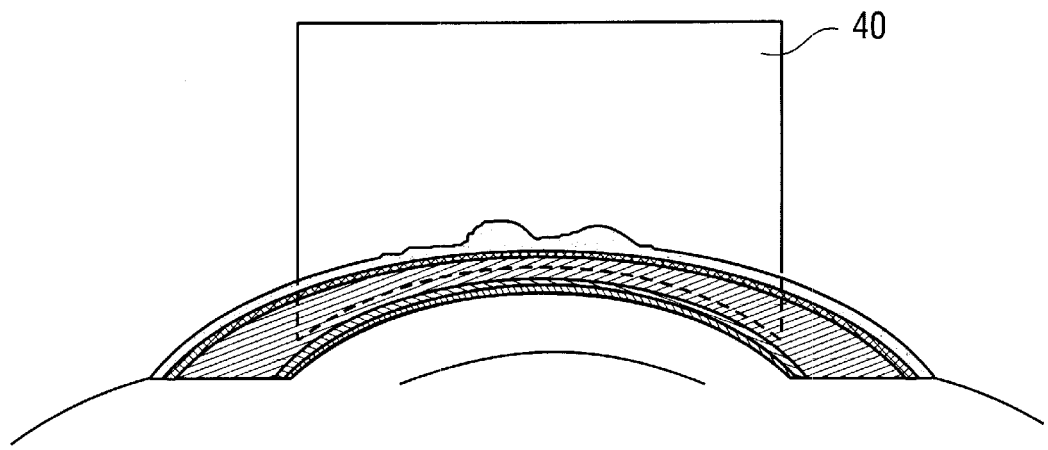
FIG. 9B shows the asymmetric application of a laser beam to the cornea of FIG. 9.
Figure 9C:
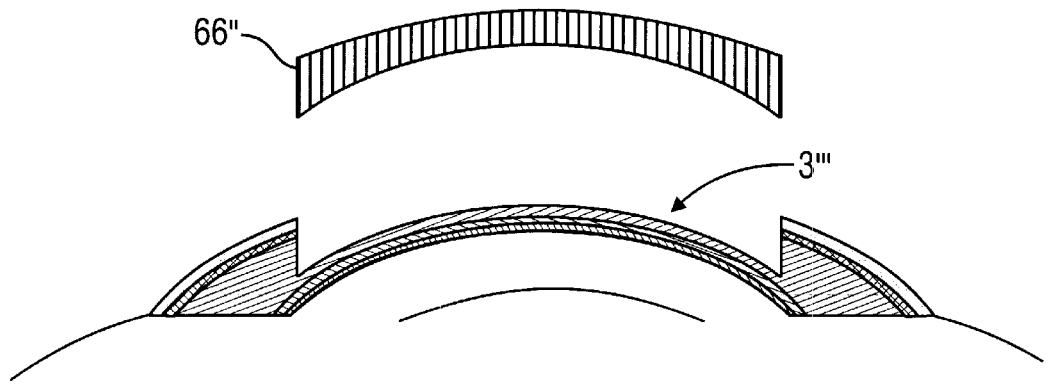
FIG. 9C shows the ablation resulting from the laser application of FIG. 9B, with the exposed stromal bed having a uniform thickness, and a disc from a donor cornea being positioned for grafting onto the exposed stromal bed.
Figure 9D:
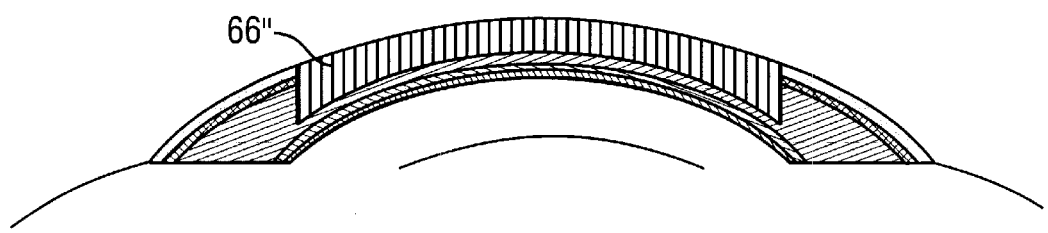
FIG. 9D shows the donor corneal disc positioned in place on the stromal bed of the receiver cornea.
Figure 9E:
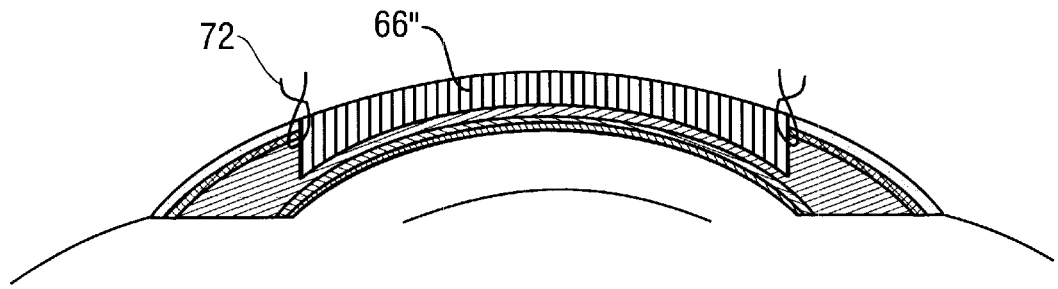
FIG. 9E shows the donor disc sutured in place for healing.

A lamellar keratoplasty procedure will now be described for correcting surface irregularities 70 on the patient's cornea, as shown in FIGS. 9 and 9A. FIG. 9B shows the asymmetric application of laser beam 40 to the cornea of FIG. 9. Once again, the laser is guided by the patient's corneal pachymetry obtained from the elevation topographer prior to the ablation, so that the extent of ablation is safely varied according to the pachymetry data across the eye. In this manner, the damaged tissue is entirely ablated but the descemet and endothelium layers of the cornea are left intact. The resulting ablation exposes corneal stromal bed 3''' having a uniform thickness, as shown in FIG. 9C. This figure also shows disc 66" ablated from a donor cornea being positioned for grafting onto the exposed stromal bed. In FIG. 9D, the donor corneal disc has been positioned in place on the stromal bed of the receiver cornea. The procedure is completed in FIG. 9E, which shows the donor disc sutured in place by sutures 72 for healing.

Figure 10:
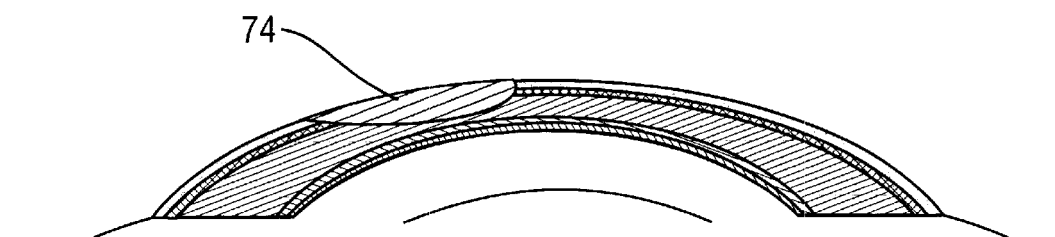
FIG. 10 is a plan view, taken in cross-section, of a cornea exhibiting an extensive defect.
Figure 10A:
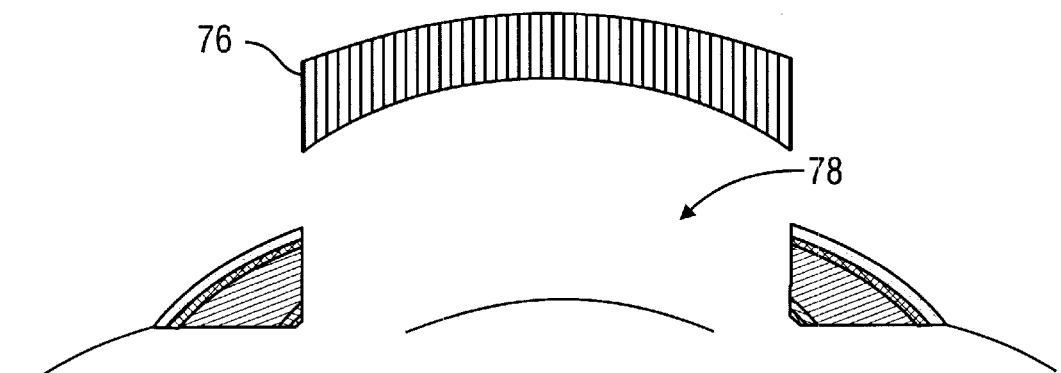
FIG. 10A illustrates an exposed ocular bed resulting from removal of the entire cornea during a deep keratoplasty procedure, and an entire donor cornea positioned for placement on the exposed bed.
Figure 10B:
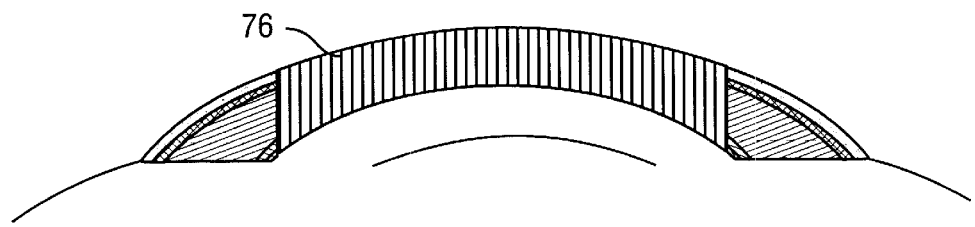
FIG. 10B shows the donor cornea of FIG. 10 positioned on the exposed ocular bed.
Figure 10C:
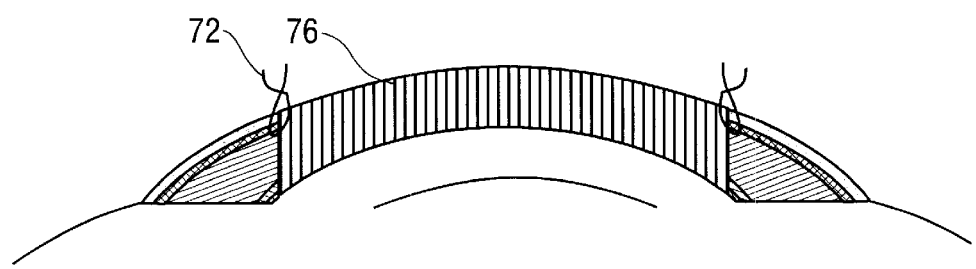
FIG. 10C shows the donor cornea sutured in place for healing.

A deep keratoplasty procedure will now be described for the correction of extensive corneal defects or irregularities 74, as represented by FIG. 10. FIG. 10A illustrates an exposed ocular bed resulting from removal of the entire cornea during a deep keratoplasty procedure. Given the dangers of such an invasive procedure, as set forth above, the corneal pachymetry is critical for safe operation of the surgical laser. FIG. 10A also shows an entire donor cornea positioned for placement on the exposed bed. FIG. 10B shows the donor cornea of FIG. 10A positioned on the exposed ocular bed, and FIG. 10C shows the donor cornea sutured in place with sutures 72 for healing.

Those of ordinary skill in the art will appreciated that the present invention differs from the above-described LASIK procedure, particularly as the present invention applies to full or partial corneal transplants. In the present invention, the anterior and posterior surfaces of a patient's cornea are mapped to obtain full pachymetry of the patient's cornea. A desirable corneal bed is identified using the patient's corneal pachymetric topographical mapping, and the mapping data is fed into the laser. The patient's ocular globe is ablated by guiding the movement and intensity of the laser according to such data; Then, a donor graft is placed on the previously prepared bed and sutured in place.

This may be contrasted with the LASIK procedure, wherein a calculated ablation based on a refractive defect is performed, and wherein the ablated tissue is never replaced. Tissue transplant or replacement is not the purpose of the LASIK procedure. This differs from a preferred application of the present invention, wherein damaged corneal tissue is discarded and replaced with healthy donor tissue seeking the reconstruction or recovery of the transparency of the previously defective cornea.

In conclusion, the surgical ablation of the present invention is designed such that the resulting ablated portion of the patient's cornea exhibits a known thickness as determined by the patient's corneal pachymetric topographical mapping. With this procedure, the transparency and refractive structure of the cornea are recovered. If, during the post-operative recovery period, the patient has a residual refractive (myopic, hyperopic, or astigmatic) defect, a LASIK procedure can be performed.

In view of the foregoing it is evident that the present invention is well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive. The scope of the invention is indicated by the claims that follow rather than the foregoing description, and all changes which come within the meaning and range of equivalence of the claims are therefore intended to be embraced therein.

What is claimed is:

1. A method of controlling the depth of corneal ablation during optical surgery, comprising the steps of:
topographically mapping the anterior and posterior surfaces of a patient's cornea to obtain full pachymetry of the patient's cornea;
identifying a desirable corneal bed using the patient's corneal pachymetric topographical mapping, wherein the desirable corneal bed is beneath a defective portion of the cornea; and
using the patient's corneal pachymetric topographical mapping to guide a surgical laser in ablating a portion of the anterior surface of the patient's cornea, including a defective portion of the cornea, to produce the desired corneal bed.

2. The method of claim 1, wherein the corneal pachymetric topographical mapping is used to identify whether the cornea exhibits refractive defects.

3. The method of claim 1, wherein the corneal pachymetric topographical mapping is used to identify structural corneal defects.

4. The method of claim 1, wherein the ablated portion of the patient's cornea exhibits a constant or known thickness.

5. The method of claim 1, wherein the desirable corneal bed exhibits a uniform or predetermined thickness thereacross.

6. The method of claim 1, further comprising the steps of:
ablating a corneal disc from the anterior surface of a donor cornea, the donor corneal disc having similar diameter and thickness to the ablated portion of the patient's cornea; and
placing the donor corneal disc onto the produced desired corneal bed of the patient's cornea.

7. The method of claim 6, wherein the thickness of the ablated portion of the patient's cornea is such that the descemet and endothelium layers are left intact.

8. The method of claim 1, wherein the mapping step is accomplished with an elevation-type corneal topography system.

9. The method of claim 8, wherein the mapping step is accomplished with an ORBSCAN topography system.

10. The method of claim 1, wherein the ablated portion of the patient's cornea exhibits a variable thickness as determined by the patient's corneal pachymetric topographical mapping.

11. The method of claim 10, wherein the thickness is varied for correction of myopia.

12. The method of claim 10, wherein the thickness is varied for correction of hyperopia.

13. The method of claim 10, wherein the thickness is varied for correction of astigmatism.

14. The method of claim 10, wherein the thickness is varied for correction of corneal ectasia.

15. The method of claim 10, wherein the thickness is varied for correction of leucoma.

16. The method of claim 10, wherein the thickness is varied for correction of corneal surface irregularities.

17. A method of ocular surgery, comprising the steps of:
mapping the anterior and posterior surfaces of a patient's cornea to obtain full pachymetric topographical mapping of the patient's cornea;
identifying a desirable corneal bed using the patient's corneal pachymetric topographical mapping;
making an incomplete lamellar cut across the cornea, leaving a corneal flap and hinge in place;
folding the corneal flap back over the corneal hinge to expose the corneal bed;
using the patient's corneal pachymetric topographical mapping to guide a surgical laser in ablating a portion of the exposed corneal bed to produce the desired corneal bed; and
replacing the corneal flap.

18. The method of claim 17, wherein the ablated portion of the patient's cornea exhibits a variable thickness as determined by the patient's corneal pachymetric topographical mapping.

19. The method of claim 18, wherein the thickness is varied for correction of myopia.

20. The method of claim 18, wherein the thickness is varied for correction of hyperopia.

21. The method of claim 18, wherein the thickness is varied for correction of astigmatism.

22. A system for controlling the depth of corneal ablation during optical surgery, comprising:
means for mapping the anterior and posterior surfaces of a patient's cornea to obtain full pachyrnetic topographical mapping of the patient's cornea;
means for identifying a desirable corneal bed using the patient's corneal pachymetric topographical mapping, wherein the desirable corneal bed is beneath a defective portion of the cornea;
a surgical laser; and
means using the patient's corneal pachymetric topographical mapping for guiding said surgical laser in ablating a portion of the anterior surface of the patient's cornea, including a defective portion of the cornea, to produce the desired corneal bed.

23. A system for ocular surgery, comprising:
a system for mapping the anterior and posterior surfaces of a patient's cornea to obtain full pachymetric topographical mapping of the patient's cornea;
means for identifying a desirable corneal bed using the patient's corneal pachymetric topographical mapping;
means for making an incomplete lamellar cut across the cornea, leaving a corneal flap and hinge in place;
a surgical laser;
means using the patient's corneal pachymetric topographical mapping for guiding said surgical laser in ablating a portion of the exposed corneal bed revealed by folding back the corneal flap to produce the desired corneal bed.

24. A system for controlling the depth of corneal ablation during optical surgery, comprising:
a system for mapping the anterior and posterior surfaces of a patient's cornea to obtain full pachymetric topographical mapping of the patient's cornea;
means using the patient's corneal pachymetric topographical mapping for identifying a desirable corneal bed;
means for ablating a corneal disc from the anterior surface of a donor cornea; a surgical laser; and
means using the patient's corneal pachymetric topographical mapping for guiding said surgical laser in ablating a portion of the anterior surface of the patient's cornea to produce the desired corneal bed, whereby the donor corneal disc can be placed onto the produced desired corneal bed of the patient's cornea.

25. The system of claim 24, wherein said surgical laser guiding means is capable of controlling the thickness of the ablated portion of the patient's cornea such that the descemet and endothelium layers are left intact.

26. The system of claim 24, wherein said mapping system includes an elevation-type corneal topography system.

27. The method of claim 26, wherein said mapping system includes an ORBSCAN topography system.

* * * * *